(12) United States Patent
Cason

(10) Patent No.: US 8,690,848 B2
(45) Date of Patent: Apr. 8, 2014

(54) CLOSURE FOR OSTOMY POUCH AND METHOD THEREOF

(75) Inventor: Johnnie R. Cason, Tampa, FL (US)

(73) Assignee: Ostosolutions, LLC, Dover, DE (US)

( * ) Notice: Subject to any disclaimer, the term of this patent is extended or adjusted under 35 U.S.C. 154(b) by 929 days.

(21) Appl. No.: 12/660,640

(22) Filed: Mar. 2, 2010

(65) Prior Publication Data

US 2011/0218508 A1    Sep. 8, 2011

(51) Int. Cl.
*A61F 5/44* (2006.01)

(52) U.S. Cl.
USPC ... 604/342; 604/332; 604/385.13; 220/495.1; 220/495.11; 383/37; 383/39; 383/60; 383/80

(58) Field of Classification Search
USPC .............. 604/342, 332, 385.13; 220/495.1, 220/495.11; 383/60, 80, 37, 39
See application file for complete search history.

(56) References Cited

U.S. PATENT DOCUMENTS

| | | | | |
|---|---|---|---|---|
| 2,595,934 A | * | 5/1952 | Ginsburg | 604/342 |
| 2,639,710 A | * | 5/1953 | Fazio | 604/342 |
| 2,721,553 A | * | 10/1955 | Perry | 604/342 |
| 3,523,534 A | | 8/1970 | Nolan | |
| 3,901,401 A | | 8/1975 | Lynn et al. | |
| 4,468,227 A | | 8/1984 | Jensen | |
| 4,533,967 A | * | 8/1985 | Conly et al. | 360/123.01 |
| 4,701,169 A | * | 10/1987 | Steer | 604/344 |
| 4,872,869 A | | 10/1989 | Johns | |
| 5,690,621 A | | 11/1997 | Canela | |
| 6,106,508 A | | 8/2000 | Lavender | |
| 6,537,261 B1 | * | 3/2003 | Steer et al. | 604/342 |
| 6,902,551 B2 | * | 6/2005 | Hansen et al. | 604/342 |
| 6,964,654 B2 | | 11/2005 | Fanti | |
| 7,468,056 B2 | | 12/2008 | Burt | |
| 7,569,038 B1 | * | 8/2009 | Salem, Jr. | 604/385.13 |
| 7,722,585 B2 | | 5/2010 | Falconer et al. | |
| 7,722,586 B2 | * | 5/2010 | Mullejans et al. | 604/342 |
| 7,745,681 B1 | | 6/2010 | Ferguson | |
| 7,819,850 B2 | * | 10/2010 | Mullejans et al. | 604/344 |
| 7,947,025 B2 | | 5/2011 | Buglino et al. | |
| 8,070,737 B2 | | 12/2011 | Cline et al. | |
| 8,092,437 B2 | | 1/2012 | Cline | |
| 8,096,980 B2 | | 1/2012 | Cline | |
| 8,100,875 B2 | * | 1/2012 | Cline et al. | 604/328 |

(Continued)

FOREIGN PATENT DOCUMENTS

GB    2 193 098 A  *  8/1986 ............ A61F 5/448

*Primary Examiner* — Tatyana Zalukaeva
*Assistant Examiner* — Ginger T Chapman
(74) *Attorney, Agent, or Firm* — Mintz Levin Cohn Ferris Glovsky and Popeo, P.C.

(57) ABSTRACT

An ostomy closure is disclosed for sealing an ostomy pouch after use and removal from an ostomy mounting plate. The ostomy mounting plate is secured to an individual. The ostomy closure comprises a cap body defining an interior surface and an exterior surface extending to a peripheral edge. A cap flange is coupled to the peripheral edge of the cap body and extends from the interior surface of the cap body. A cap locking member is integral to the cap flange. A cap lip defining an interior surface and an exterior surface extends from the cap flange for manipulating the cap body and the cap flange. The cap flange couples with a pouch flange of the ostomy pouch for defining a sealing closure for maintaining the stool and the stool odor within the ostomy chamber and a locking closure for preventing inadvertent removal of the cap flange from the pouch flange.

17 Claims, 20 Drawing Sheets

(56) References Cited

U.S. PATENT DOCUMENTS

| | | | |
|---|---|---|---|
| 8,105,298 B2 * | 1/2012 | Mullejans et al. | 604/332 |
| 8,142,406 B2 | 3/2012 | Blum | |
| 8,343,121 B2 * | 1/2013 | Cramer et al. | 604/344 |
| 2002/0077611 A1 | 6/2002 | Von Dyck et al. | |
| 2002/0114539 A1 | 8/2002 | Strevey et al. | |
| 2002/0133134 A1 * | 9/2002 | Wilbon | 604/385.13 |
| 2003/0023210 A1 * | 1/2003 | Bedard et al. | 604/332 |
| 2004/0059306 A1 * | 3/2004 | Tsal et al. | 604/332 |
| 2004/0087920 A1 * | 5/2004 | Etheredge, III | 604/332 |
| 2004/0111072 A1 | 6/2004 | McKissick | |
| 2004/0191459 A1 | 9/2004 | Driesten | |
| 2005/0182379 A1 * | 8/2005 | Olsen et al. | 604/385.13 |
| 2005/0247432 A1 * | 11/2005 | Bhatti et al. | 165/80.3 |
| 2007/0080092 A1 * | 4/2007 | DeLuca | 206/554 |
| 2008/0004580 A1 * | 1/2008 | Mullejans et al. | 604/344 |
| 2008/0039809 A1 | 2/2008 | Kamen et al. | |
| 2008/0243098 A1 * | 10/2008 | Hewitt | 604/355 |
| 2009/0163883 A1 | 6/2009 | Christensen et al. | |
| 2009/0247969 A1 | 10/2009 | Nishtala et al. | |
| 2009/0299309 A1 * | 12/2009 | Fenton | 604/336 |
| 2010/0022976 A1 | 1/2010 | Weig | |
| 2010/0069859 A1 | 3/2010 | Weig | |
| 2010/0100064 A1 | 4/2010 | Sambasivam | |
| 2010/0174253 A1 | 7/2010 | Cline | |
| 2010/0211033 A1 | 8/2010 | Blum | |
| 2011/0028924 A1 | 2/2011 | Murray | |
| 2011/0040269 A1 | 2/2011 | Cline | |
| 2011/0071485 A1 | 3/2011 | Foley et al. | |
| 2011/0092929 A1 | 4/2011 | Weig | |
| 2011/0118684 A1 | 5/2011 | Nguyen-Demary | |
| 2011/0178483 A1 | 7/2011 | Oberholtzer et al. | |
| 2011/0213321 A1 | 9/2011 | Fattman et al. | |
| 2011/0213322 A1 | 9/2011 | Cramer | |
| 2011/0313378 A1 | 12/2011 | Gregory | |
| 2012/0109086 A1 | 5/2012 | Tsai | |
| 2012/0179124 A1 | 7/2012 | Nguyen-Demary | |
| 2013/0144236 A1 * | 6/2013 | Brandt et al. | 604/344 |

* cited by examiner

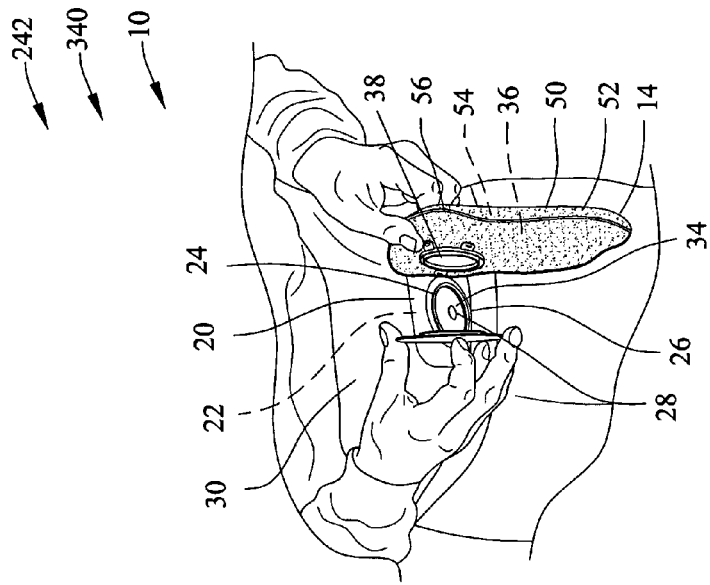
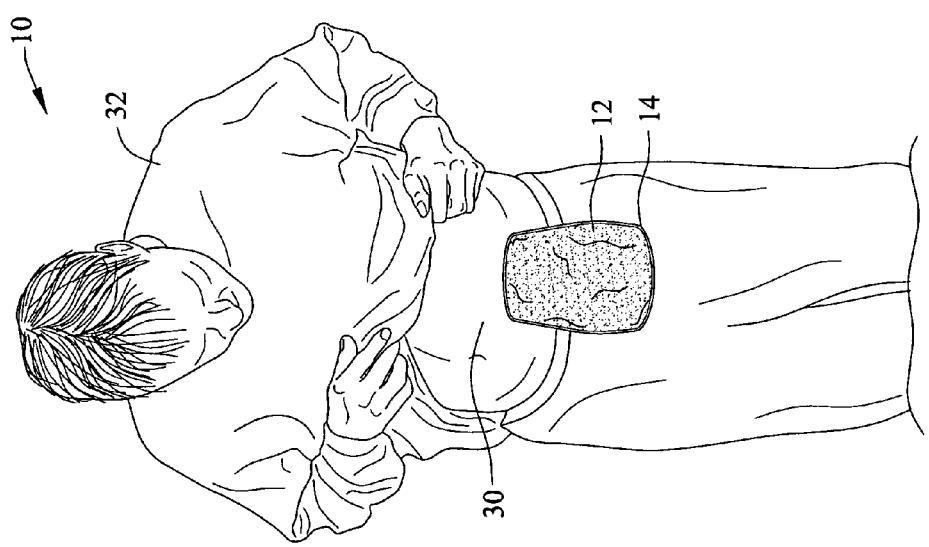
FIG. 1
FIG. 2

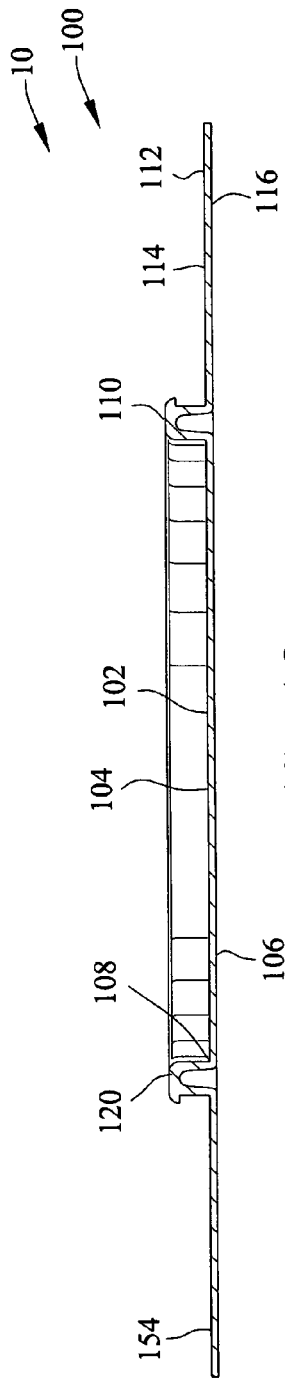
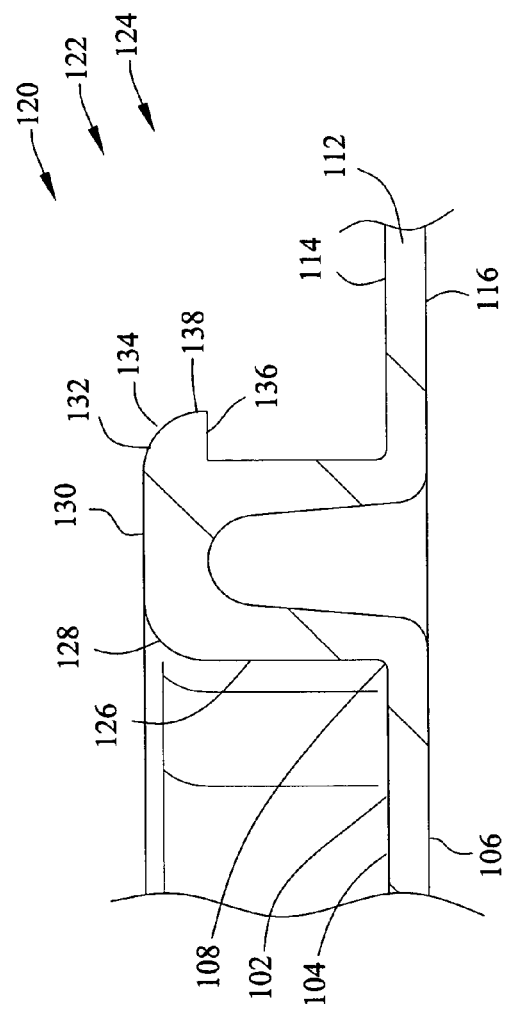
FIG. 12
FIG. 13

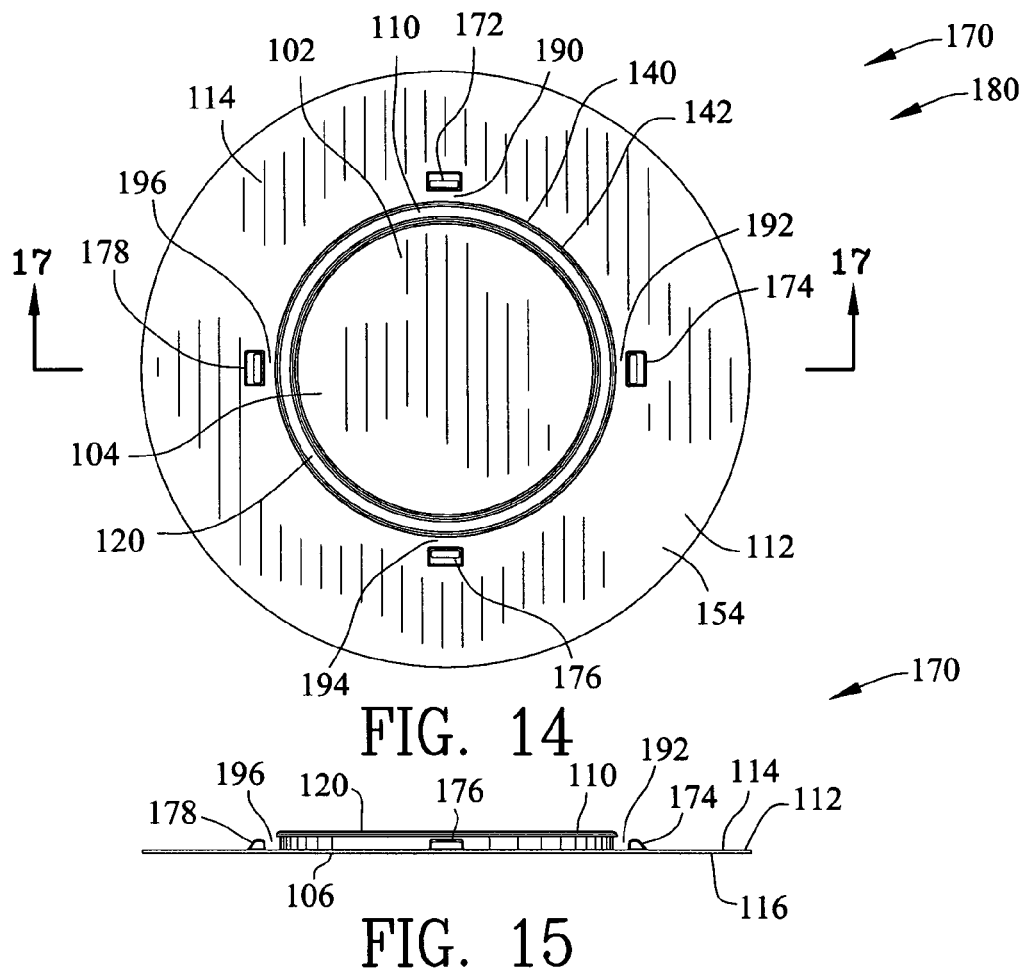
FIG. 14
FIG. 15
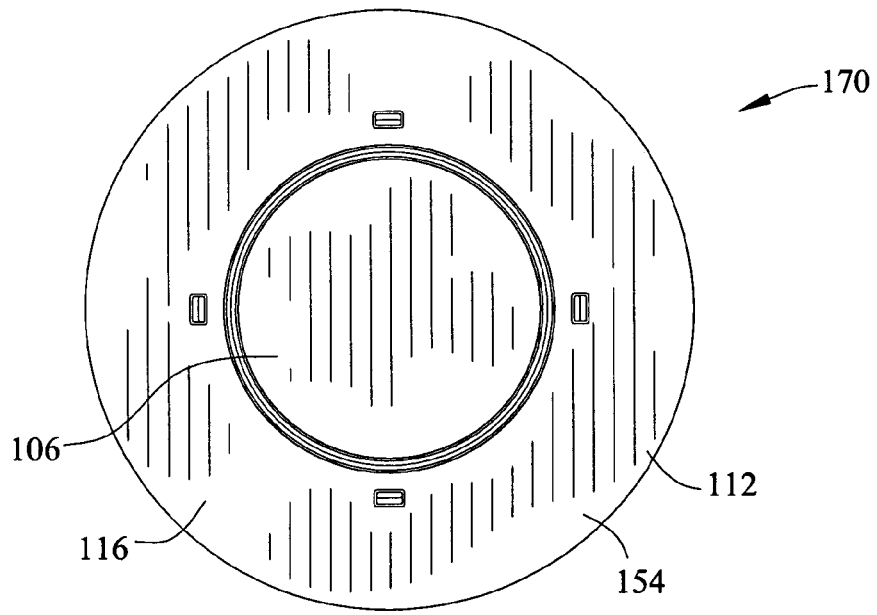
FIG. 16

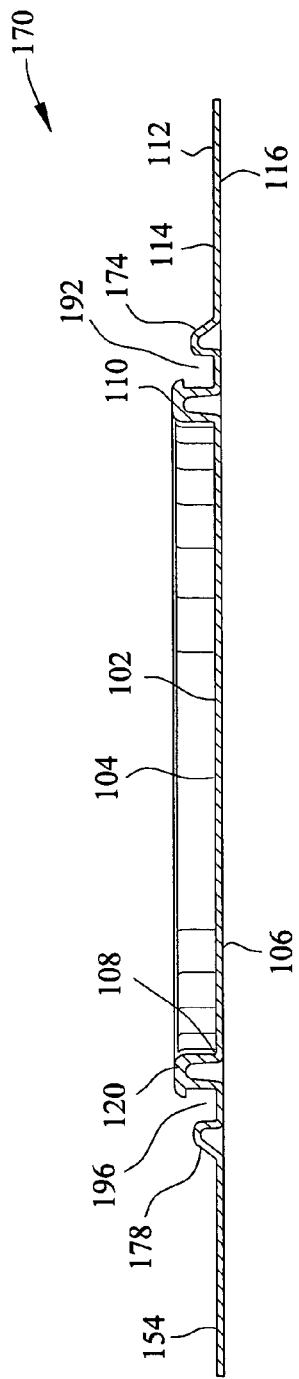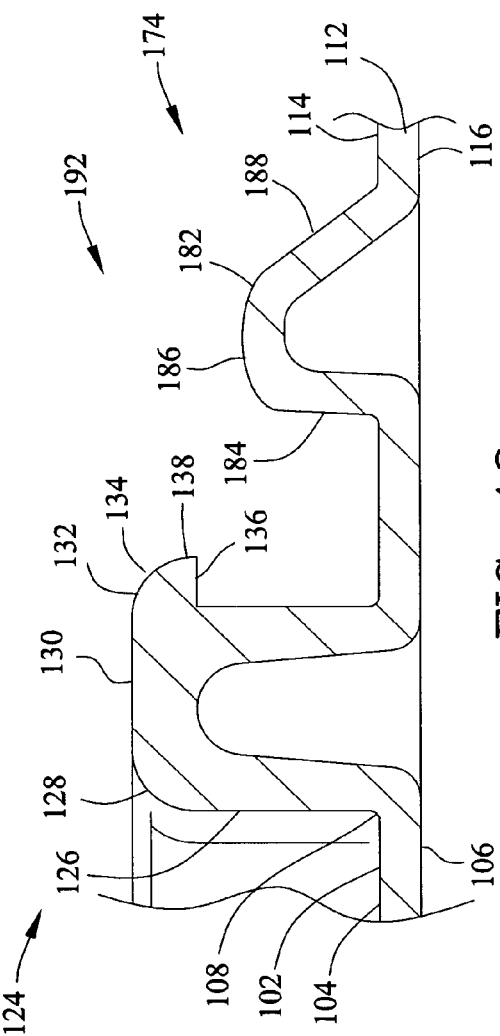

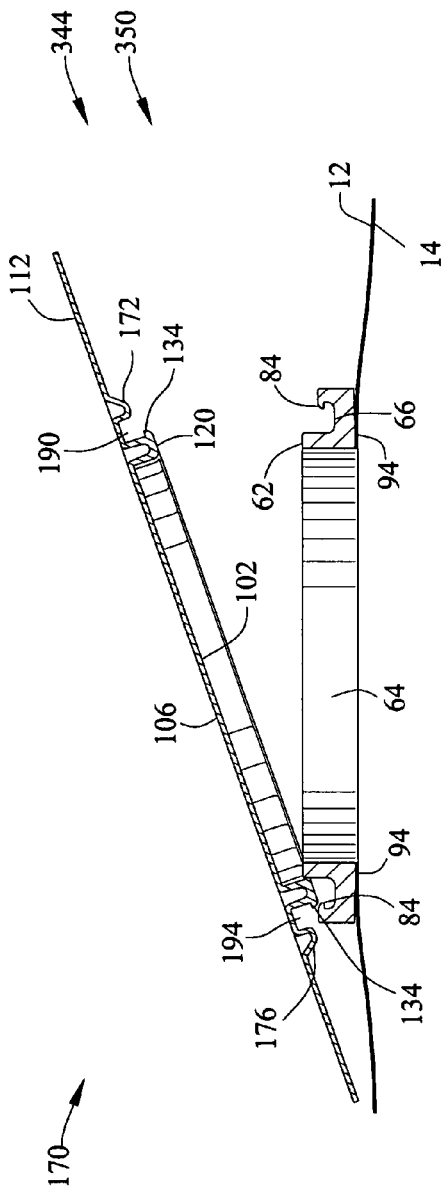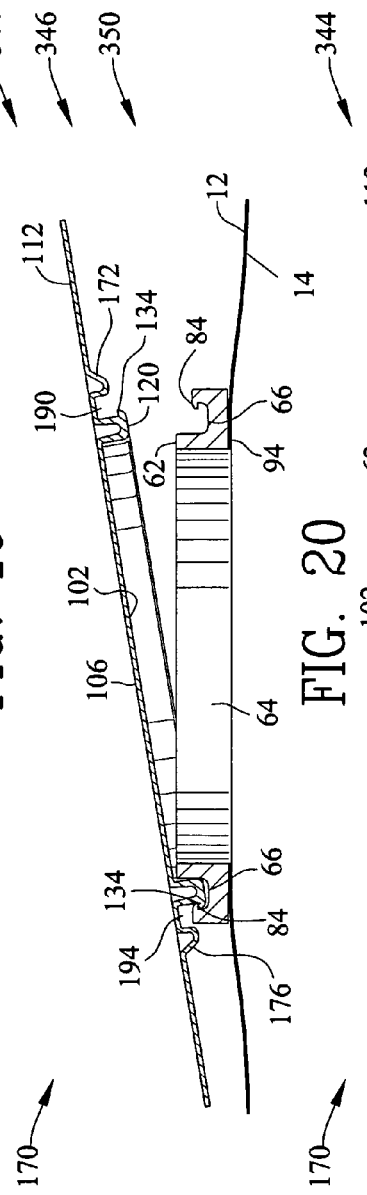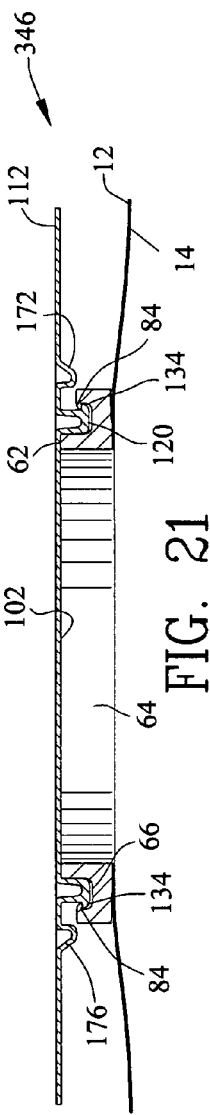

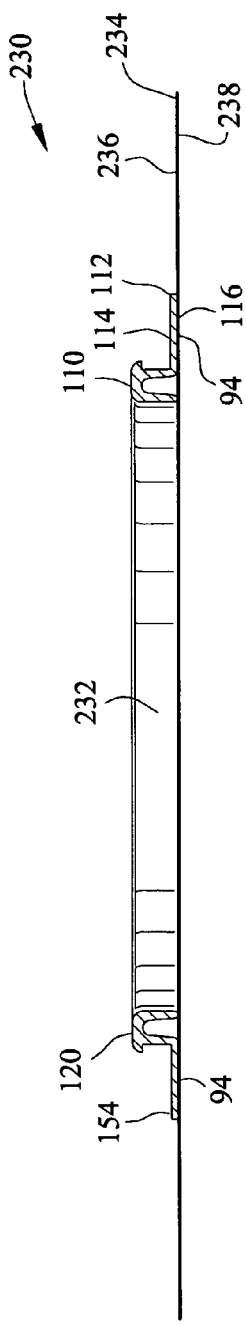
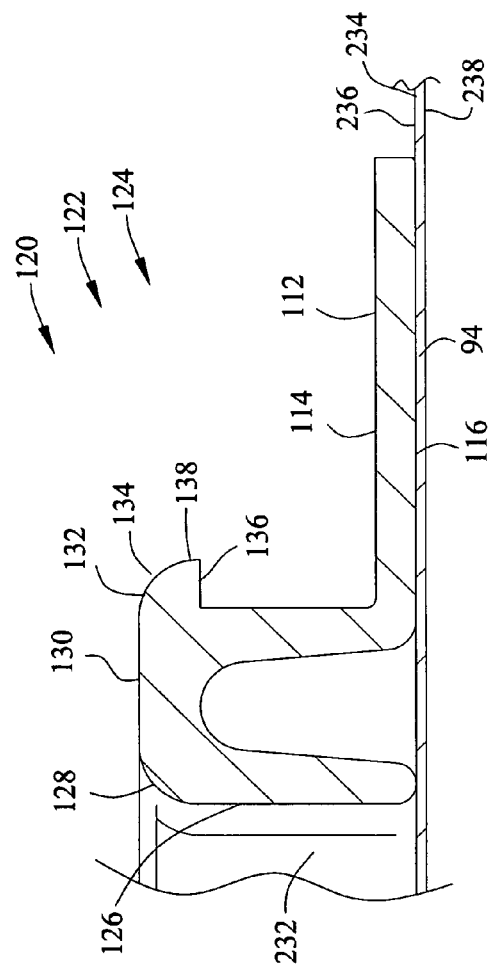
FIG. 31
FIG. 32

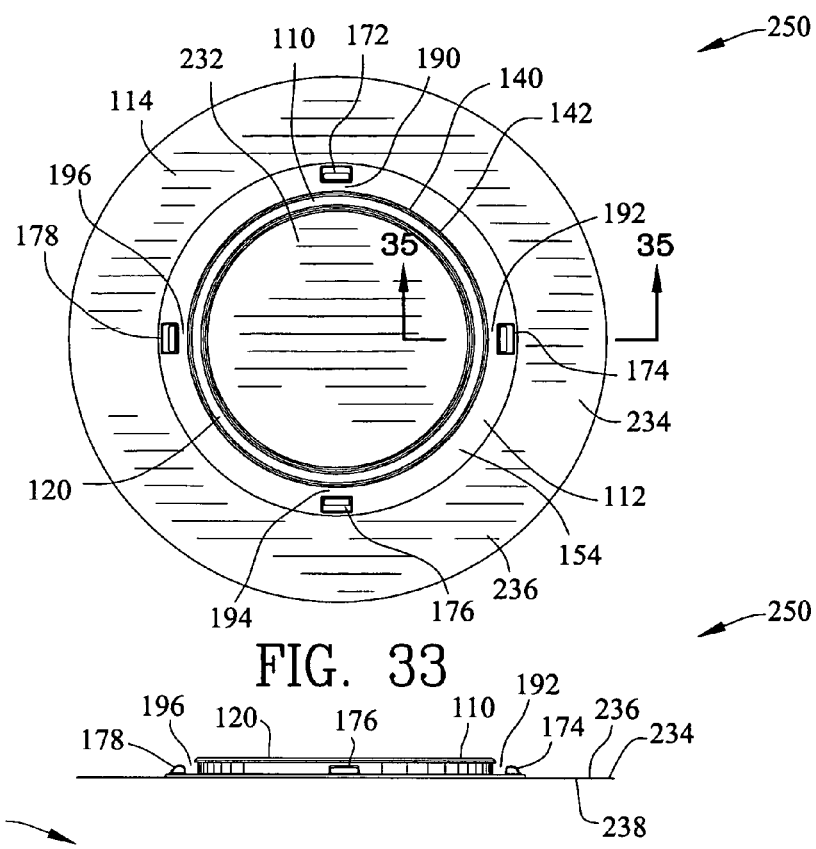
FIG. 33
FIG. 34
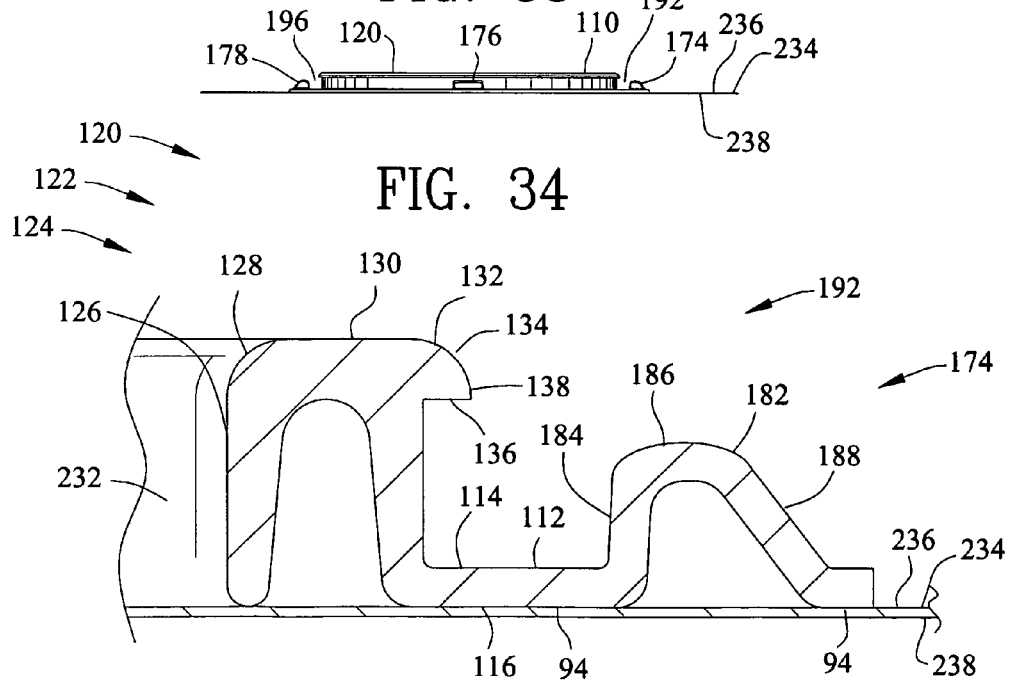
FIG. 35

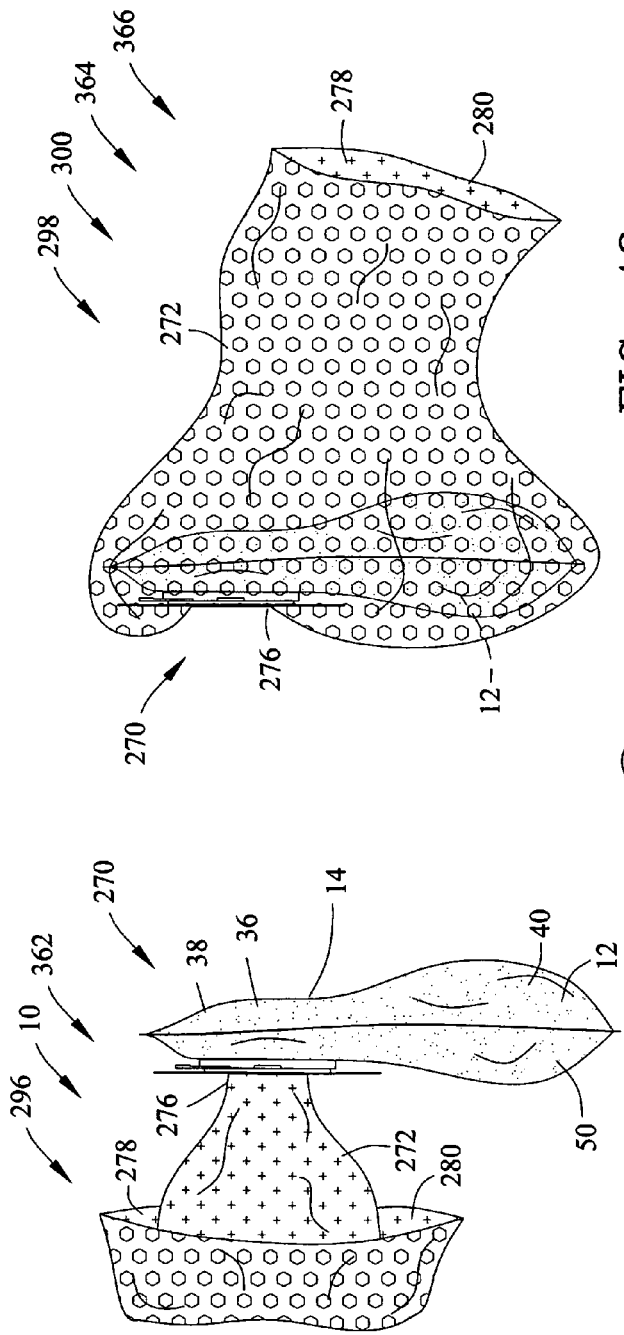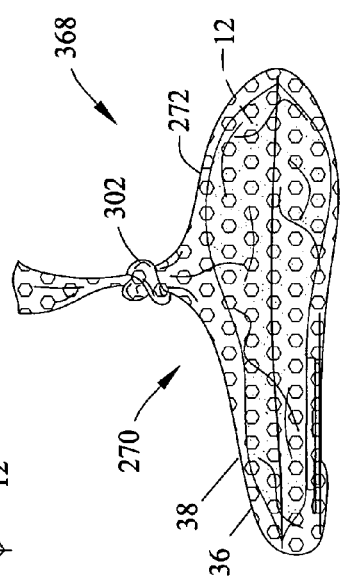

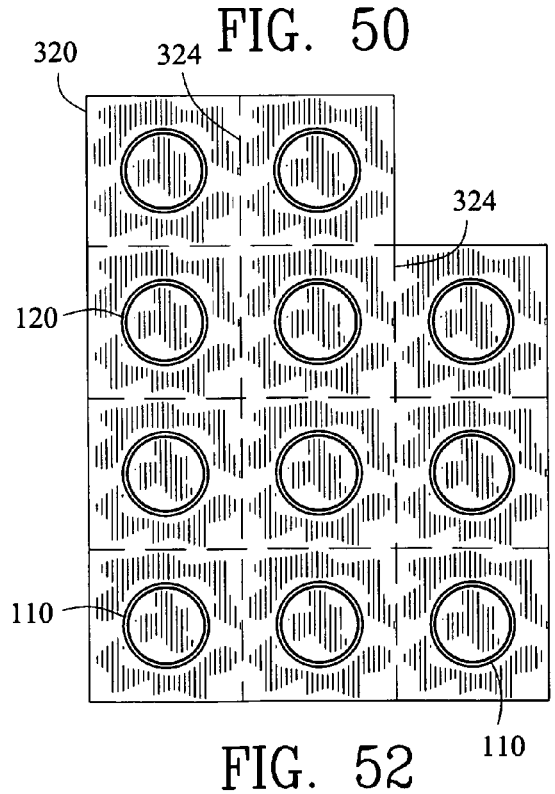
FIG. 50
FIG. 51
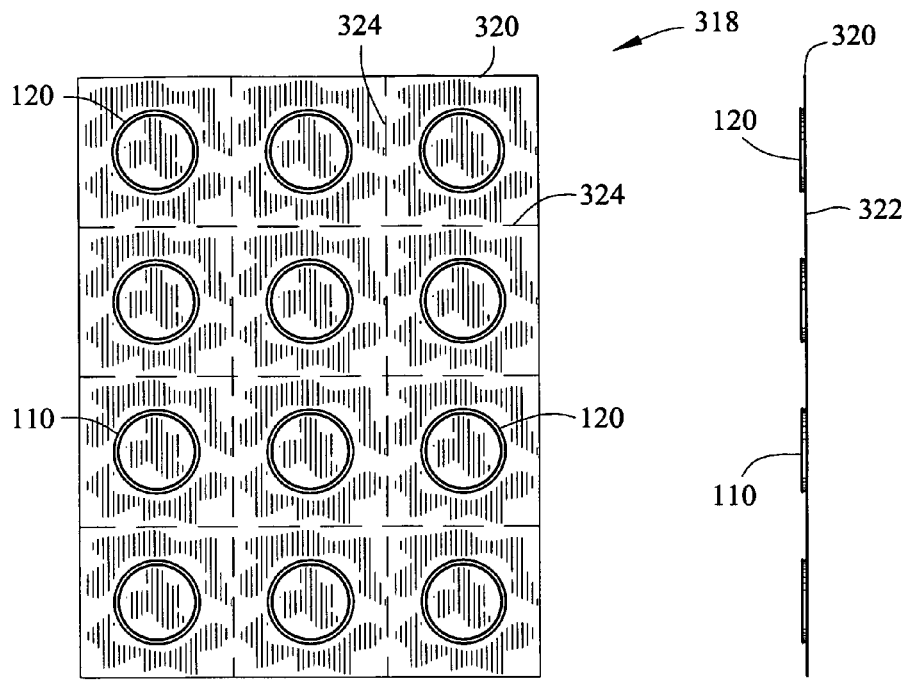
FIG. 52
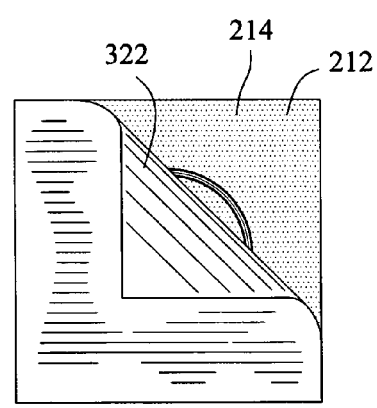
FIG. 53

CLOSURE FOR OSTOMY POUCH AND METHOD THEREOF

BACKGROUND OF THE INVENTION

1. Field of the Invention

This invention relates to closures and more particularly to an improved ostomy pouch closure.

2. Background of the Invention

Due to various intestinal or rectal diseases such as cancer or inflammatory bowel disease, many people require a surgical procedure whereby the diseased portion of the intestine is removed and the healthy portion of the intestine is attached to the abdominal wall. Surgical diversion procedures involving the small intestine are referred to as illeostomies and those involving the large intestine or rectum are referred to as colostomies. The end of the intestine or rectum is sutured to the skin forming a stoma. Waste products which are discharged from the stoma are collected using an ostomy appliance. An ostomy appliance conventionally includes a wafer and an ostomy pouch.

Ostomy pouches are secured to the skin of the wearer by a sealing material, or wafer, which extends around the stoma. The appliance may be designed as a one-piece device with a wafer attaching directly to the wearer and then connecting to a pouch with a drain at the lower end. This device is reusable until the wearer needs to replace the entire appliance.

Alternately, the pouch may be manufactured in two pieces. The first piece is a separate wafer with a central opening sized to fit around the stoma. This wafer has a flange in varying sizes to accommodate a wide range of stoma sizes and has adhesive properties that allow it to be affixed to the wearer over the stoma. The second piece, or ostomy pouch, has a corresponding flange that snaps into the wafer flange. The ostomy pouch has a flexible wall with an opening to receive waste products from the stoma.

The two piece ostomy pouch may be either closed-end, such that the pouch must be replaced after each use, or be drainable, such that the pouch can be reused until the wearer needs to replace it, usually after a day or two. The drainable pouches have a tapered open end to allow the user to discharge the stool into a conventional toilet and then seal the pouch using a specially designed clip or other closure.

The drainable pouches have the disadvantage of being cumbersome to empty the stool contents, carry a on-going risk of clip or closure failure resulting in embarrassing leads, and very messy to empty the contents in a hygienic manner. However, the advantage of the drainable pouch is that the waste contents are deposited directly in the toilet and disposed of normally from that point.

The advantages of the closed-end pouches is that they are designed for one-time usage, which makes them ideal for everyday use, special occasions or for intimate moments. This eliminates the need to manipulate a tail clip or closure to empty the pouch and there is no need for messy draining of stool or an uncomfortable clip to worry about. These pouches can be emptied much faster and a toilet area is preferable but not required. The user simply removes the pouch and discards it in a trash receptacle. The disadvantage of this system is that the used pouches cannot be flushed down a toilet and must be discarded in the trash. As a result, the user is faced with the embarrassing challenge of disposing of a highly odorous pouch numerous times per day. This is a difficult challenge in the privacy of one's home and especially so in the workplace, restaurants, and other social settings. Several devices of the prior art have met with varying degrees of success in solving these problems. None, however completely satisfies the requirements for a complete solution to the aforestated problems. The following U.S. patents are attempts of the prior art to solve these problems.

U.S. Pat. No. 3,901,401 to Lynn, et al discloses a safety closure for containers wherein the neck of the container has a continuous encircling rib and the closure has an internal bead formation which snaps over the rib. The rib on the container has a portion of reduced radius to facilitate snapping the closure off of the container. The container has a flange which lies below the closure and has a notched portion which defines the release position of the closure. The closure has a tab which is not accessible due to the presence of the flange on the container excepting when the tab is in alignment with the notch. There are protuberances on either the continuous rib of the container or the interior of the closure which take up the slack in a radial direction normally present due to manufacturing tolerance.

U.S. Pat. No. 4,468,227 to Jensen discloses a wound drainage device in the form of a flexible pouch having top and bottom walls and having pleated side walls that allow the top wall to be lifted a limited distance without transmitting appreciable lifting or tensioning forces to the bottom wall when the bottom wall is surgically apertured and secured about a wound site. The top wall includes an access opening having a flanged locking ring of flexible plastic extending thereabout. A removable closure cap is attached to the access opening, the cap having a flat rim of flexible plastic with circumferential locking ribs releasably and sealingly engaging a series of mating ribs provided by the flanged portion of the ring.

U.S. Pat. No. 4,872,869 to Johns discloses a low profile ostomy device includes an ostomy POUCH with an opening, a first coupling member attached to the ostomy pouch at the opening, and a second coupling member for attachment to a user's body. The first and second coupling members are engaged by the joining of an engaging element on each of the members, the engagement providing a tight mechanical seal between the members within the ostomy pouch.

U.S. Pat. No. 5,690,621 to Canela discloses a drainable pouch for colostomy patients with a stoma and that includes a valve for selectively releasing the gases trapped within the pouch. The valve assembly is removably mounted permitting a user to rinse the interior of the pouch from the uppermost portion. The valve also contains an odor suppresant filter that may include an impregnated fragrance. A cap member is used to cover the outlet spout. A sheet having cooperative dimensions and made out of a non-transparent material is used to conceal said pouch from public view.

U.S. Pat. No. 6,106,508 to Lavender discloses an ostomy pouch having a first and second panels of flexible material sealed to each around the edges to form a pouch, and a aperture for receiving waste product from a stoma. A seal is provided on the inner surfaces of the two panels to seal waste products in the pouch before the pouch is removed from the side of a wearer.

U.S. Pat. No. 6,964,654 to Fanti discloses a disposable cover for enclosing the outlet spout of a drainable stoma pouch. The cover includes front and rear walls sealed along side and bottom edges, with an unsealed upper edge. Preferably, one or more stiffening ribs extend longitudinally across the front and rear walls near the unsealed upper edge. The presence, spacing and relative orientation of such ribs on the external surfaces of the front and rear walls render the disposable cover self-opening such that it may be easily placed over to enclose the outlet spout of a drainable stoma pouch. Once positioned, the cover is clamped onto the tail section of the pouch to provide effective odor and moisture containment therein.

U.S. Pat. No. 7,468,056 to Burt discloses a colostomy pouch with a vent and a method for venting gas collected in the colostomy pouch. A dual vent and cap assembly attached to a colostomy pouch vents gas trapped in the pouch either continuously or as periodically desired by a user. A method for venting gas collected in the colostomy pouch provides that replacement and/or cleaning of the colostomy pouch is reduced. Also, a method of using a disposable sleeve in combination with a clip may be used to hygienically clean the colostomy pouch.

United States Patent Application 2004/0111072 to McKissick discloses a display arrangement for organizing and presenting supplies and implements needed for ostomy care has at least one display surface for the supplies and implements, the display surface having alphamerically sequenced indicia disposed thereon. The indicia include at least one indicator for at least one skin preparation product, at least one indicator for stoma measurement, at least one indicator for at least one wafer cutting implement, at least one indicator for a wafer, at least one indicator for at least one adhesive product; and at least one indicator for at a pouch.

Although the aforementioned prior art have contributed to the development of the art of securing an object to a support member, none of these prior art patents have solved the needs of this art.

Therefore, it is an object of the present invention to provide an improved apparatus for the sealing and disposal of an ostomy pouch.

Another object of this invention is to provide an improved apparatus for sealing the ostomy pouch following its removal from the stoma of a patient in an odor free manner.

Another object of this invention is to provide an improved apparatus for maintaining a stool and order released from the stool within the ostomy pouch to facilitate the odor proof disposal of the used ostomy pouch.

Another object of this invention is to provide an improved apparatus for the hygienic disposal of an ostomy pouch and its contents following the removal from the stoma of a colostomy patient.

Another object of this invention is to provide an improved apparatus that is simple for the colostomy patient to use.

Another object of this invention is to provide an improved apparatus that is easy to cost effectively produce.

The foregoing has outlined some of the more pertinent objects of the present invention. These objects should be construed as being merely illustrative of some of the more prominent features and applications of the invention. Many other beneficial results can be obtained by modifying the invention within the scope of the invention. Accordingly other objects in a full understanding of the invention may be had by referring to the summary of the invention, the detailed description describing the preferred embodiment in addition to the scope of the invention defined by the claims taken in conjunction with the accompanying drawings.

SUMMARY OF THE INVENTION

The present invention is defined by the appended claims with specific embodiments being shown in the attached drawings. For the purpose of summarizing the invention, the invention relates to an ostomy closure for sealing an ostomy pouch after use and removal from an ostomy mounting plate. The ostomy mounting plate is secured to an individual. A plate flange is secured to the ostomy mounting plate. A plate locking member is integral to the plate flange. A plate orifice is positioned within the plate flange and traverses the ostomy mounting plate. The ostomy pouch has a first flexible layer coupling to a second flexible layer for defining an ostomy chamber. A pouch flange is secured to the first flexible layer. A pouch locking member is integral to the pouch flange. A pouch orifice is positioned within the pouch flange and traverses the first flexible layer. The pouch flange engages with the plate flange and the pouch locking member engages with the plate locking member for conveying stool from the individual to the ostomy chamber. The stool releasing a stool odor. The pouch flange disengages with the plate flange for dispose of the stool. The ostomy closure comprises a cap body defining an interior surface and an exterior surface extending to a peripheral edge. A cap flange couples to the peripheral edge of the cap body and extends from the interior surface of the cap body. A cap locking member is integral to the cap flange. A cap lip defines an interior surface and an exterior surface extending from the cap flange for manipulating the cap body and the cap flange. The cap flange couples with the pouch flange for positioning the cap body over the pouch orifice and defines a sealing closure. The sealing closure maintains the stool and the stool odor within the ostomy chamber. The cap locking member engages with the pouch locking member for defining a locking closure. The locking closure prevents inadvertent removal of the cap flange from the pouch flange.

In a more specific embodiment of the invention, the interior surface of the cap lip includes an aligning tab positioning adjacent to the cap flange. The aligning tab and the cap flange define an aligning channel there between for centering the cap flange relative to the pouch flange prior to the cap flange coupling within the pouch flange.

In another more specific embodiment of the invention, the exterior surface of the cap body includes a cap adhesive layer for temporarily securing the cap body to the ostomy pouch.

In another more specific embodiment of the invention, a flexible storage bag has an enclosure body extending between a bag base and a bag opening. The enclosure body defines a bag chamber. The bag base couples to the exterior surface of the cap body for defining a cap and bag single unit. The enclosure body compacts adjacent to the exterior surface of the cap body for defining a temporary compact cap and bag unit. The enclosure body expands from the exterior surface of the cap body for defining a deployed cap and bag unit. The bag opening retracts over the flexible storage bag for defining an inverted flexible storage bag. The bag opening retracts over the cap body for defining a bag cap enclosure. The bag opening retracts over the ostomy pouch for defining a bag pouch enclosure. A bag closure engages the enclosure body for encapsulating both the cap body and the ostomy pouch within the bag chamber.

In one embodiment of the invention, the cap flange defines a cap flange aperture. A flexible sheet defines an interior surface and an exterior surface. The interior surface of the flexible sheet is coupled to the cap flange for covering the cap flange aperture. The cap flange couples with the pouch flange for positioning the flexible sheet over the pouch orifice and defining a sealing closure. The sealing closure maintains the stool within the ostomy chamber. The cap locking member engages with the pouch locking member for defining a locking closure. The locking closure prevents inadvertent removal of the cap flange from the pouch flange.

In another embodiment of the invention, a sheet of ostomy closures for sealing a plurality of ostomy pouches. The plurality of ostomy closures engage with the plurality of ostomy pouches after removal from an ostomy mounting plate. The sheet of ostomy closures comprises a plurality of cap bodies defining an interior surface and an exterior surface extending to a peripheral edge. A plurality of cap flanges are coupling to the peripheral edge of the plurality of cap bodies and extend from the interior surface of the plurality of cap bodies. A plurality of cap locking members are integral to the plurality of cap flanges. A plurality of cap lips define an interior surface and an exterior surface extending from the plurality of cap flanges for manipulating the plurality of cap bodies and the plurality of cap flanges. A perforated edge traverses the plurality of cap bodies for assisting in the separation of each of the plurality of cap bodies. Each of the plurality of cap flanges couple with the pouch flange for positioning each of the plurality of cap bodies over the pouch orifice and defining a sealing closure. The sealing closure maintains the stool within the ostomy chamber. Each of the plurality of cap locking members engage with the pouch locking member for defining a locking closure. The locking closure prevents inadvertent removal of the plurality of cap flanges from the pouch flange.

The invention is also incorporated into the method of utilizing an ostomy closure for sealing an ostomy pouch. The method comprises the steps of disengaging the pouch locking member from the plate locking member. The pouch flange is disengaged from the plate flange. The cap flange is engaged with the pouch flange for positioning the cap body over the pouch orifice and maintaining the stool and the stool odor within the ostomy chamber. The cap locking member is engaged with the pouch locking member for preventing inadvertent removal of the cap flange from the pouch flange.

The foregoing has outlined rather broadly the more pertinent and important features of the present invention in order that the detailed description that follows may be better understood so that the present contribution to the art can be more fully appreciated. Additional features of the invention will be described hereinafter which form the subject of the claims of the invention. It should be appreciated by those skilled in the art that the conception and the specific embodiments disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a fuller understanding of the nature and objects of the invention, reference should be made to the following detailed description taken in connection with the accompanying drawings in which:

FIG. 1 is a front view of an individual having an ostomy pouch engaging an abdominal wall;

FIG. 2 is an enlarged portion of FIG. 1, illustrating the ostomy pouch removed from an ostomy mounting plate and a first embodiment for an ostomy closure incorporating the present invention;

FIG. 12 is a sectional view along line 12-12 in FIG. 9;

FIG. 13 is an enlarged portion of FIG. 12;

FIG. 14 is a top view of a second embodiment for an ostomy closure including an aligning tab for defining an aligning channel between the aligning tab and a cap flange;

FIG. 15 is a side view of FIG. 14;

FIG. 16 is a bottom view of FIG. 14;

FIG. 17 is a sectional view along line 17-17 in FIG. 14;

FIG. 18 is an enlarged portion of FIG. 17;

FIG. 19 is a view similar to FIG. 17 illustrating an aligning channel centering the ostomy closure relative to a pouch flange on the ostomy pouch;

FIG. 20 is a view similar to FIG. 19 illustrating a cap flange of the ostomy closure coupling with the pouch flange of the ostomy pouch;

FIG. 21 is a view similar to FIG. 20 illustrating a cap locking member of the ostomy closure engaging a pouch locking member of the pouch flange;

FIG. 31 is a sectional view along line 28-28 in FIG. 28;

FIG. 32 is an enlarged portion of FIG. 31;

FIG. 33 is a top view of a fifth embodiment for an ostomy closure ostomy closure including an flexible sheet coupled to the cap flange for covering the cap flange aperture and an aligning tab for defining an aligning channel between the aligning tab and a cap flange;

FIG. 34 is a side view of FIG. 33;

FIG. 35 is an enlarged sectional view along line 35-35 in FIG. 33;

FIG. 47 is a view similar to FIG. 46 illustrating a bag opening of the flexible storage bag retracting over the flexible storage bag;

FIG. 48 is a view similar to FIG. 47 illustrating the bag opening of the flexible storage bag retracting over the ostomy closure and the ostomy pouch;

FIG. 49 is a view similar to FIG. 48 illustrating a bag closure engaging the flexible storage bag for encapsulating both the ostomy closure and the ostomy pouch;

FIG. 50 is a top view of an eighth embodiment for a sheet of ostomy closures;

FIG. 51 is a side view of FIG. 50;

FIG. 52 is a view similar to FIG. 50 wherein a single ostomy closure has been removed along a perforated edge; and FIG. 53 is a rear view of the single ostomy closure removed from FIG. 52 wherein an adhesive backing sheet is being removed from a cap adhesive layer;

Similar reference characters refer to similar parts throughout the several Figures of the drawings.

DETAILED DISCUSSION

Figure 3:
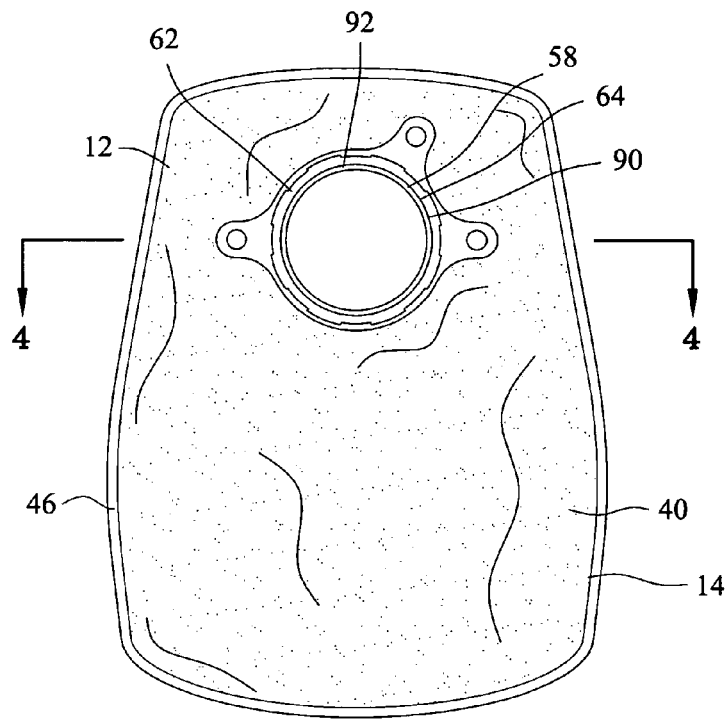
FIG. 3 is a front view of the ostomy pouch incorporating prior art.
Figure 4:
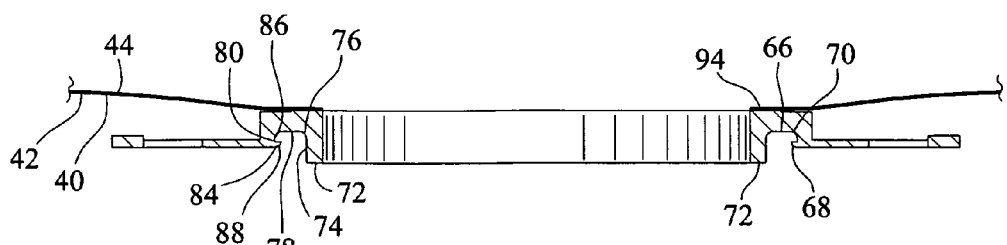
FIG. 4 is a sectional view along line 4-4 in FIG. 3 incorporating prior art.
Figure 5:
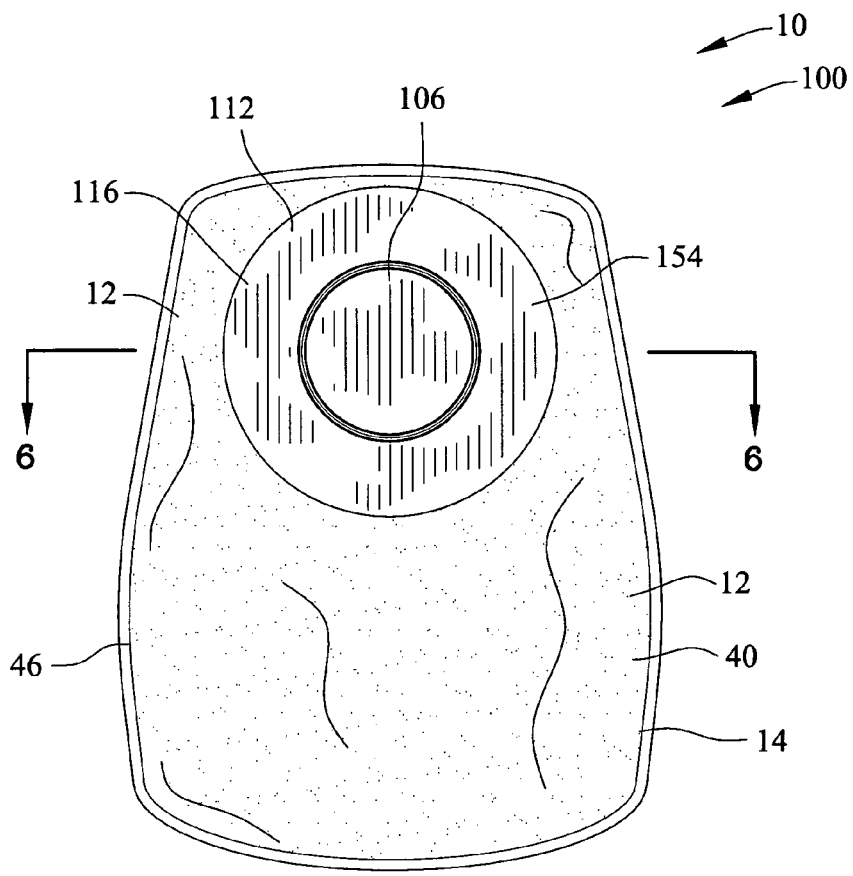
FIG. 5 is a view similar to FIG. 3 having the ostomy closure engaging the ostomy pouch.

FIGS. 1-53 are multiple embodiments for an ostomy closure 10 for sealing an ostomy pouch 12 after use and removal from an ostomy mounting plate 20. Both the ostomy pouch 12 and the ostomy mounting plate 20 constitute prior art. As best shown in FIGS. 1 and 2, the ostomy pouch 12 is coupled to the abdominal wall 30 of an individual 32 by the ostomy mounting plate 20. The ostomy mounting plate 20 is secured to an abdominal wall 30 of an individual 32 by an adhesive plate layer 22. The ostomy mounting plate 20 includes a plate flange 24. A plate locking member 26 is integral to the plate flange 24. A plate orifice 28 is positioned within the plate flange 24 and traverses the ostomy mounting plate 20. The plate orifice 28 is aligned with a stoma 34 located in the abdominal wall 30.

As shown in FIGS. 1-4, the ostomy pouch 12 has a first flexible layer 40 and a second flexible layer 50. The first flexible layer 40 includes an exterior surface 42 and an interior surface 44 extending to a first layer edge 46. The second flexible layer 50 includes an exterior surface 52 and an interior surface 54 extending to a second layer edge 56. The first layer edge 46 and the second layer edge 56 are coupled by a heat sealing, gluing or other coupling means 94. The first layer edge 46 and the second layer edge 56 define an ostomy chamber 60. The first flexible layer 40 includes a pouch aperture 58 for access to the ostomy chamber 60. As shown in FIGS. 1-6, 26, 27, 40, 41 and 45-49, the ostomy pouch 12 may include a closed-end ostomy pouch 14.

A pouch flange 62 is securing to the exterior surface 42 of the first flexible layer 40. The pouch flange 62 includes a pouch orifice 64 wherein the pouch orifice 64 is aligned with the pouch aperture 58. The pouch flange 62 further includes a pouch sealing member 66 and a pouch locking member 68. The pouch sealing member 66 comprises a first generally I-shaped mating member 70. More specifically, the pouch sealing member 66 extends from a pouch seal rim 72 and surface 72, a first linear member and surface 74, a primary arcuate member and surface 76, a second linear member and surface 78, to a secondary arcuate member and surface 80. The pouch locking member 68 is integral to the pouch flange 62 and comprises a first locking tab 84 extending from the secondary arcuate member 80. More specifically, the first locking tab 84 extends from a main linear lock member 86 to a main arcuate lock member 88. The pouch flange 62 is shown to include a circular configuration 90 providing the first generally 3-shaped mating member 70 and the pouch locking member 82 with an annular configuration 92.

As shown in FIGS. 1 and 2, the pouch flange 62 engages with the plate flange 24 and the pouch locking member 68 engages with the plate locking member 26 for coupling the ostomy pouch 12 to the plate flange 24 and for conveying stool 36 from the individual 32 to the ostomy chamber 60. The stool 36 releases a stool odor 38. The pouch flange 62 disengages with the plate flange 24 for dispose of the stool 36. Upon the removal of the ostomy pouch 12 from the ostomy mounting plate 20, the pouch orifice 64 is exposed where the stool 36 may escape from the ostomy pouch 12.

FIGS. 2-13 illustrate a first embodiment 100 of the ostomy closure 10 for maintaining the stool 36 and the stool odor 38 within the ostomy chamber 60. The first embodiment 100 of the ostomy closure 10 comprises a cap body 102 defining an interior surface 104 and an exterior surface 106 extending to a peripheral edge 108. A cap flange 110 is coupled to the peripheral edge 108 of the cap body 102 and extends from the interior surface 104 of the cap body 102. A cap lip 112 defining an interior surface 114 and an exterior surface 116 extend from the cap flange 110 for manipulating the cap body 102 and the cap flange 110.

The cap flange 110 further includes a cap sealing member 120 and a cap locking member 122. The cap sealing member 120 comprises a second generally J-shaped mating member 124. More specifically, the cap sealing member 120 extends from the interior surface 104 of the cap body 102, a third linear member and surface 126, a major arcuate member and surface 128, a fourth linear member and surface 130, to a minor arcuate member and surface 132. The cap locking member 122 is integral to the cap flange 110 and comprises a second locking tab 134 extending from the minor arcuate member 132. More specifically, the second locking tab 134 extends from a minor linear lock member 136 to a minor arcuate lock member 138. The cap flange 110 is shown to include a circular configuration 140 providing the second generally J-shaped mating member 124 and the cap locking member 122 with an annular configuration 142.

Figure 6:
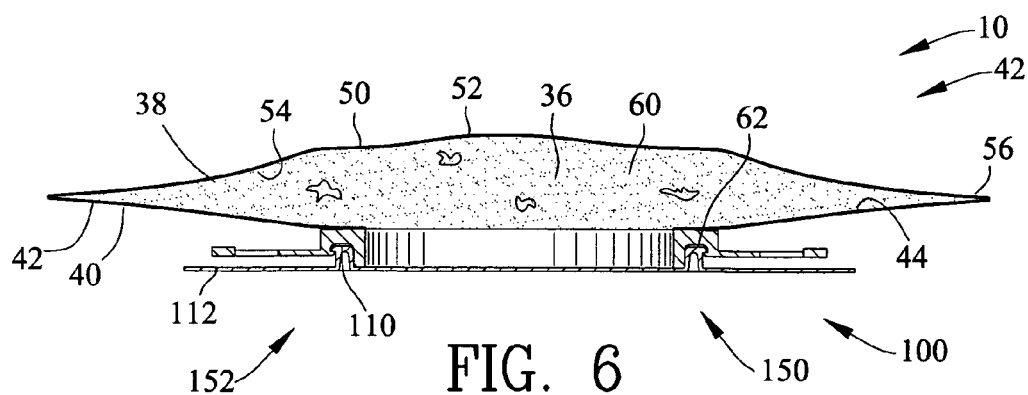
FIG. 6 is a sectional view along line 6-6 in FIG. 5.
Figure 7:
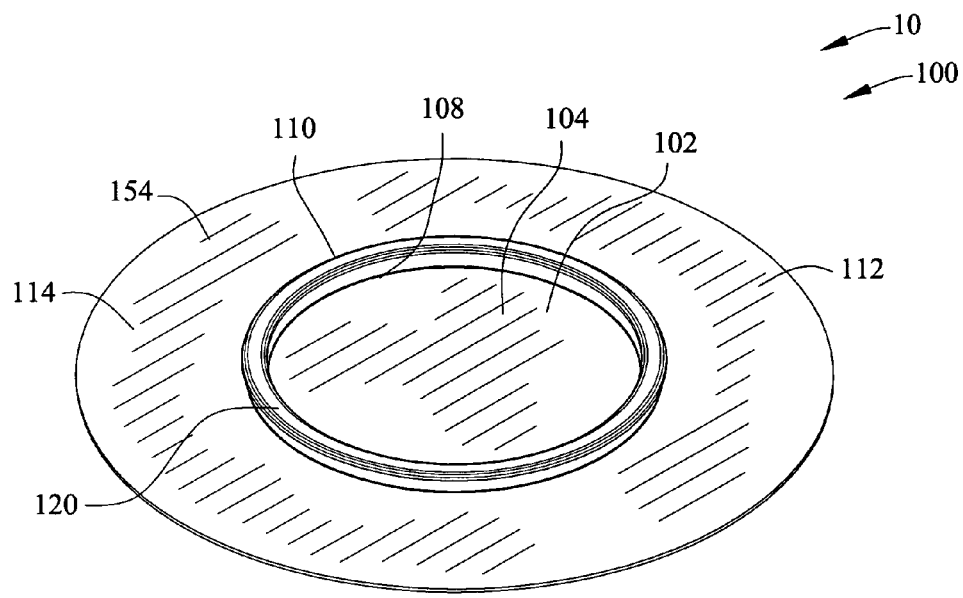
FIG. 7 is a top isometric view of the ostomy closure of FIGS. 2 and 5.
Figure 8:
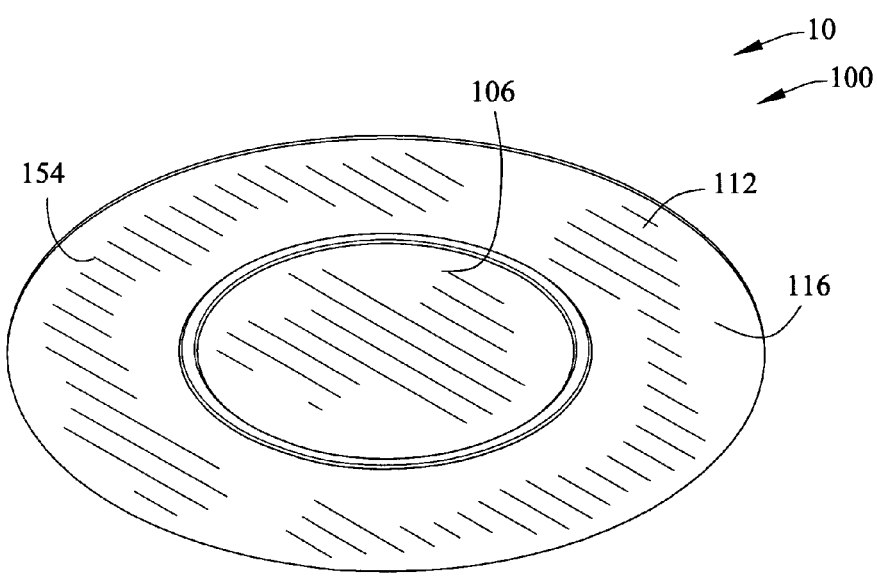
FIG. 8 is a bottom isometric view of FIG. 7.
Figure 9:
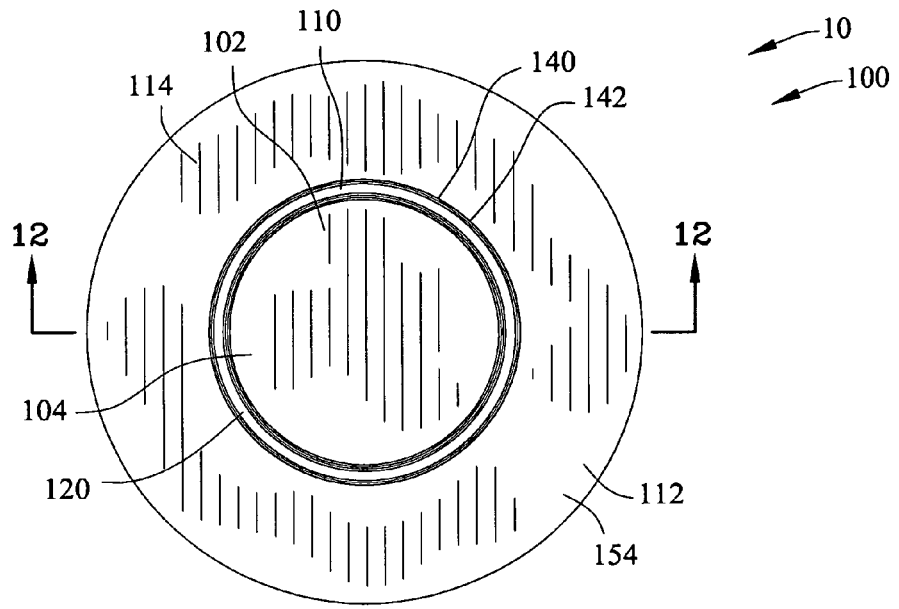
FIG. 9 is a top view of FIG. 7.
Figure 10:
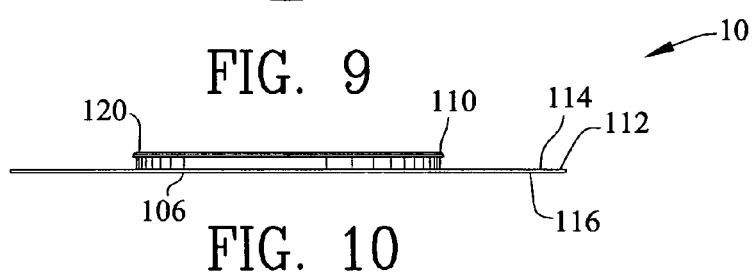
FIG. 10 is a side view of FIG. 9.
Figure 11:
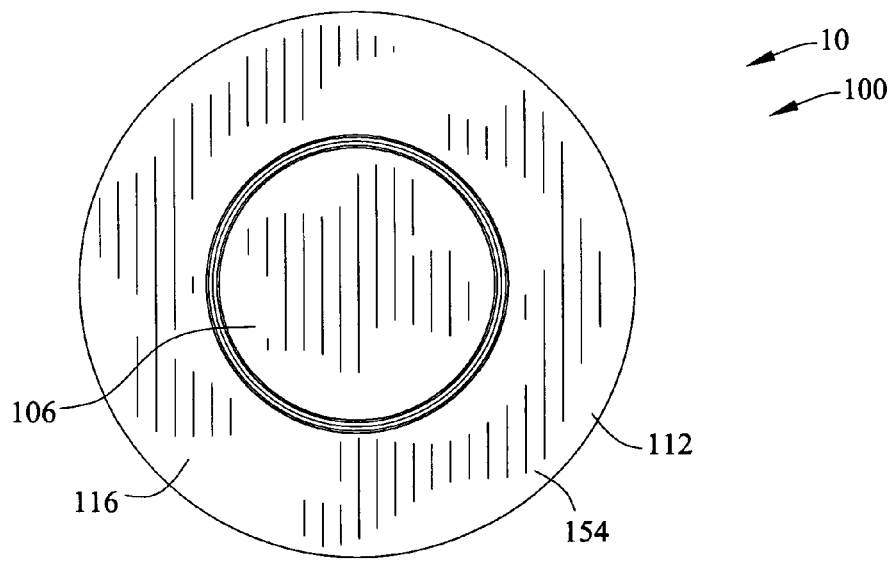
FIG. 11 is a bottom view of FIG. 9.
Figure 22:
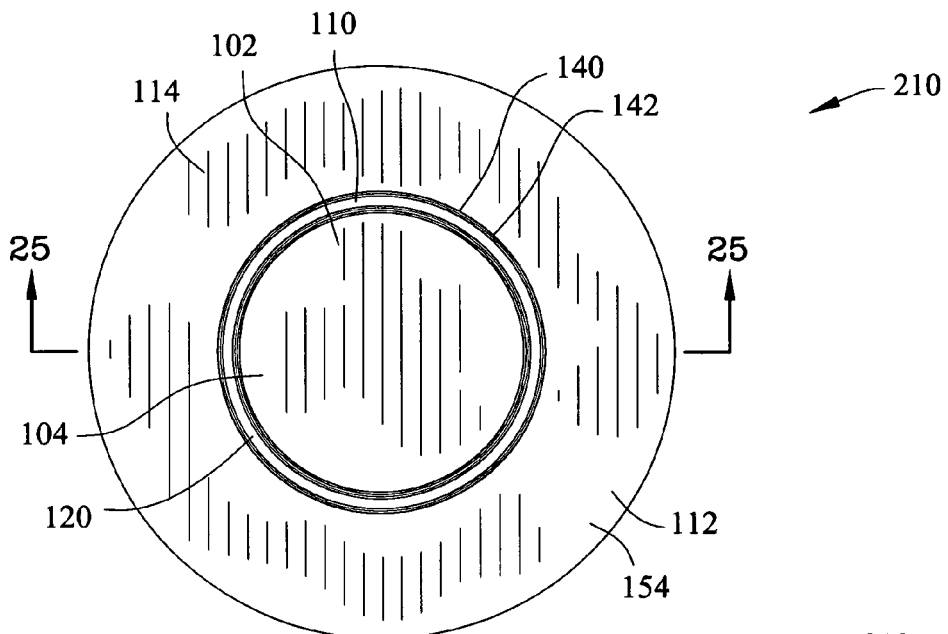
FIG. 22 is a top view of a third embodiment for an ostomy closure including a cap adhesive layer for temporarily securing the ostomy closure to the ostomy pouch.
Figure 23:
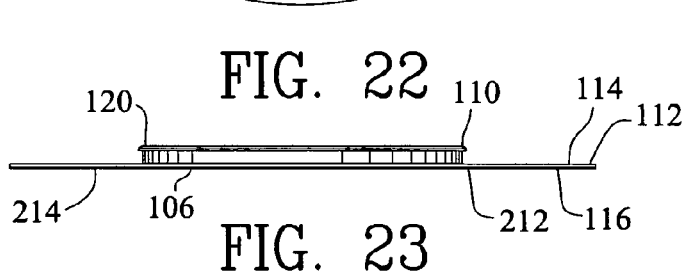
FIG. 23 is a side view of FIG. 22.
Figure 24:
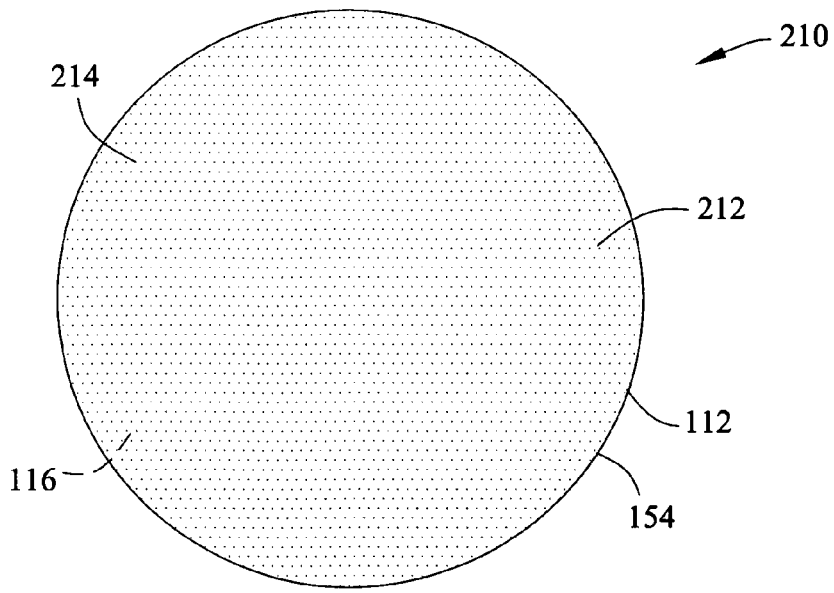
FIG. 24 is a bottom view of FIG. 22.
Figure 25:
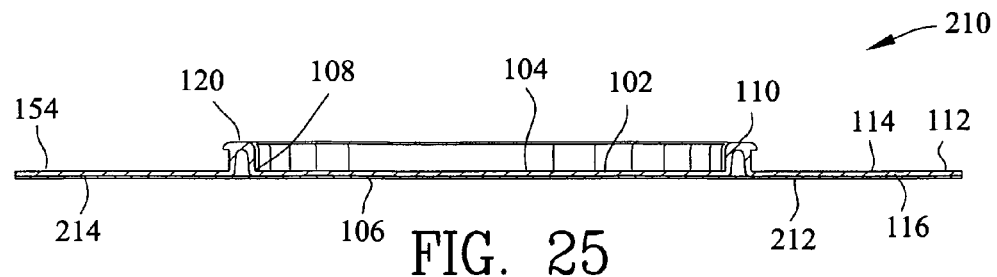
FIG. 25 is a sectional view along line 25-25 in FIG. 22.
Figure 26:
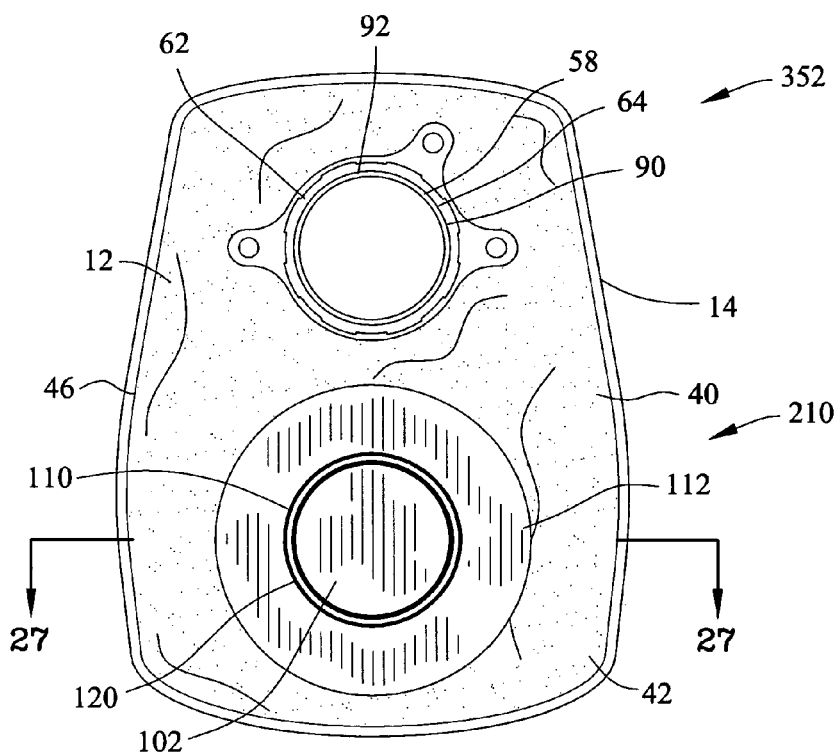
FIG. 26 is a view similar to FIG. 3 illustrating the ostomy closure of FIG. 22 wherein the cap adhesive layer temporarily securing the ostomy closure to the ostomy pouch.
Figure 27:
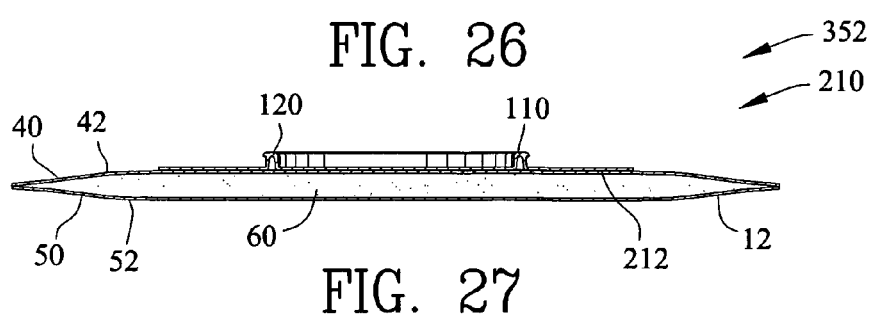
FIG. 27 is a sectional view along line 27-27 in FIG. 26.
Figure 28:
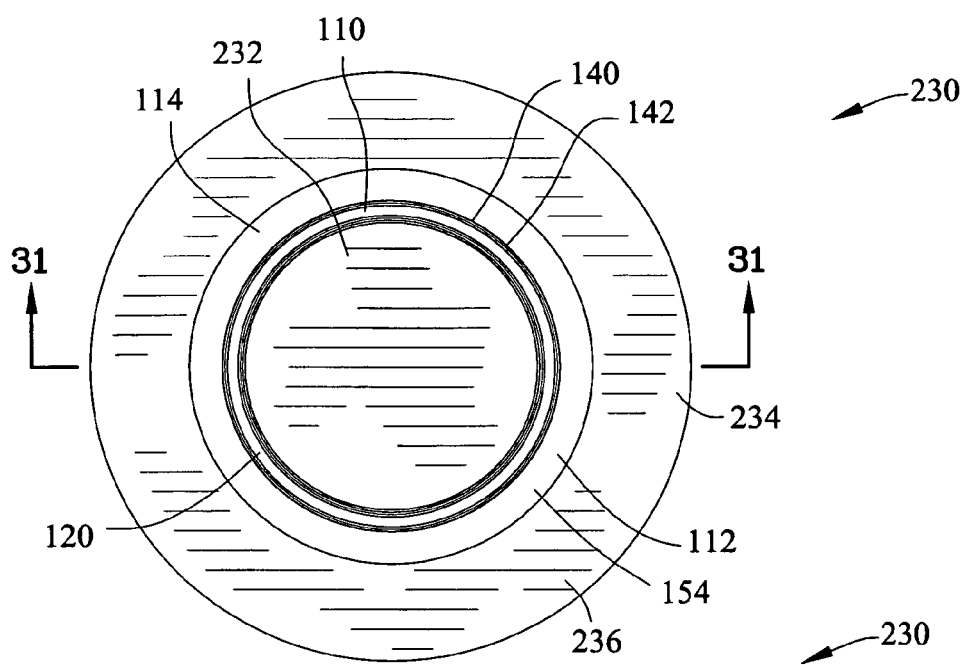
FIG. 28 is a top view of a fourth embodiment for an ostomy closure including a flexible sheet coupled to the cap flange for covering a cap flange aperture.
Figure 29:
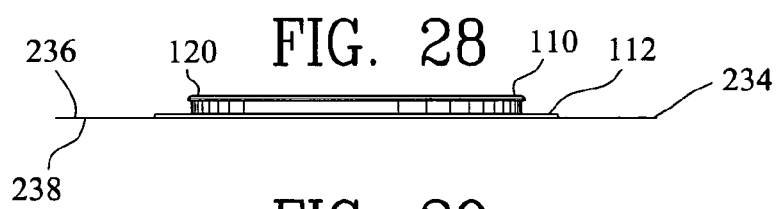
FIG. 29 is a side view of FIG. 28.
Figure 30:
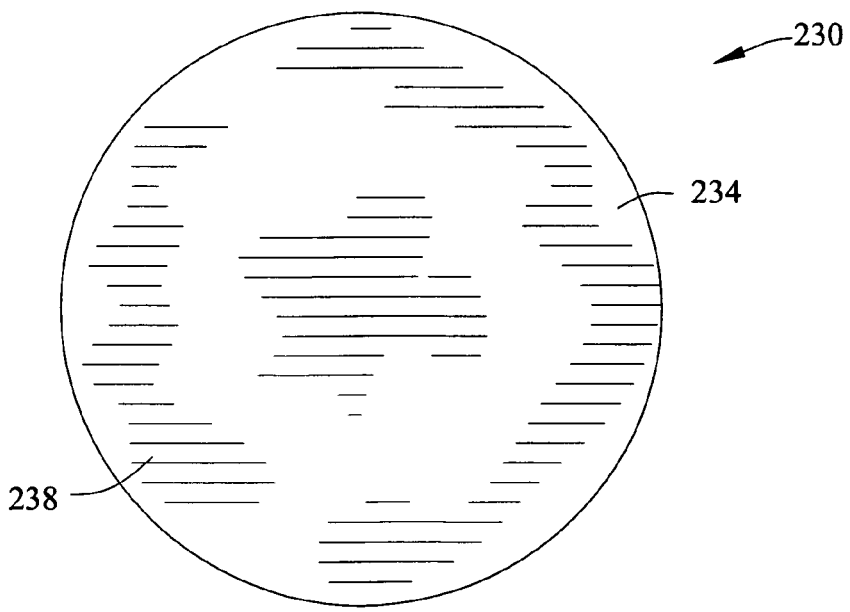
FIG. 30 is a bottom view of FIG. 28.
Figure 36:
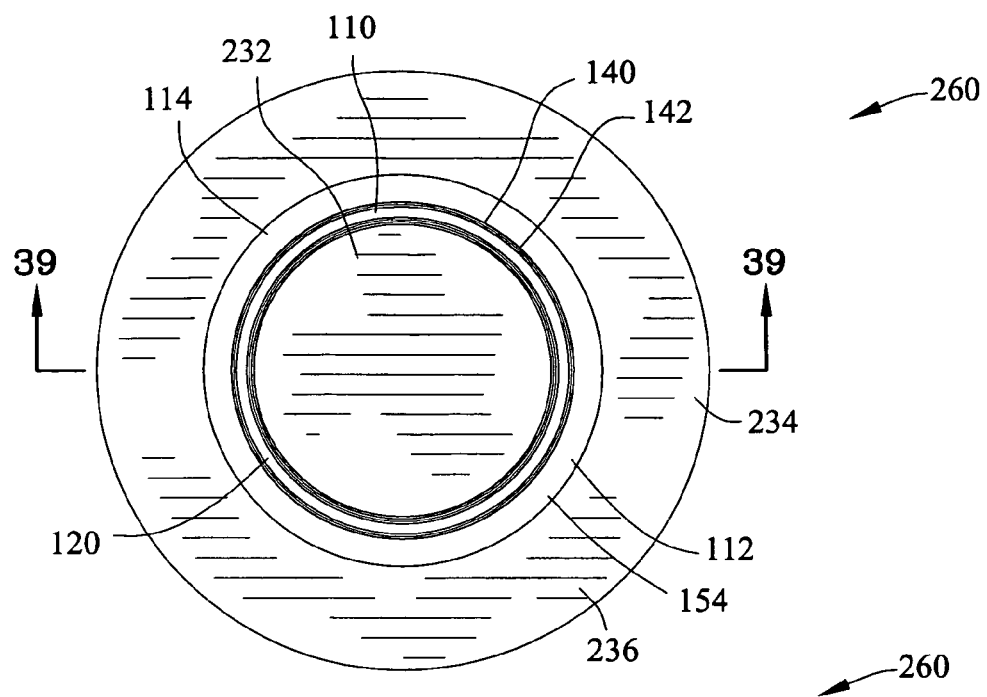
FIG. 36 is a top view of a sixth embodiment for an ostomy closure including an flexible sheet coupled to the cap flange for covering the cap flange aperture and a cap adhesive layer for temporarily securing the ostomy closure to the ostomy pouch.
Figure 37:
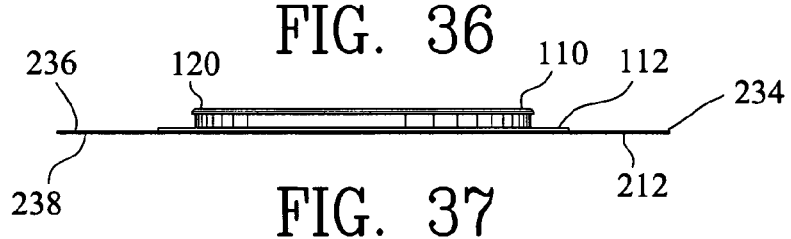
FIG. 37 is a side view of FIG. 36.
Figure 38:
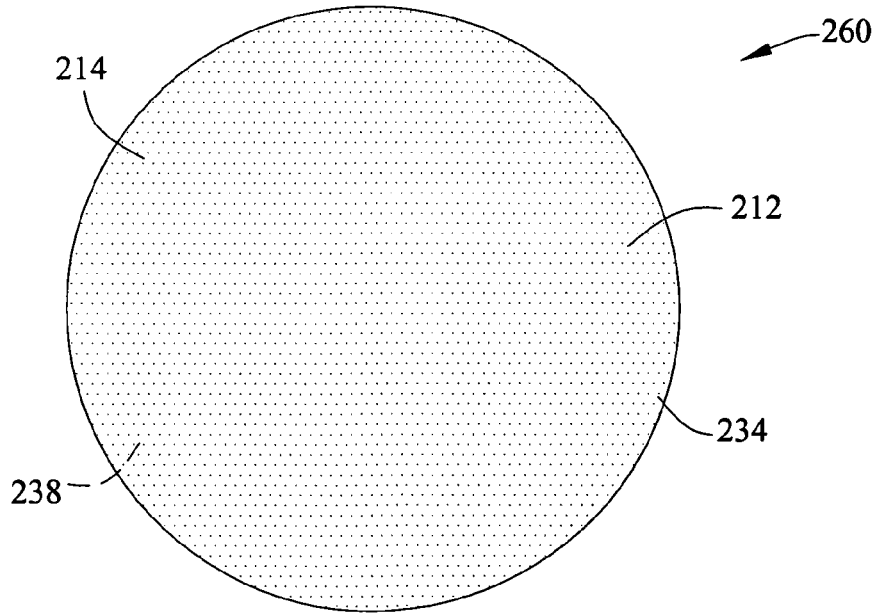
FIG. 38 is a bottom view of FIG. 36.
Figure 39:
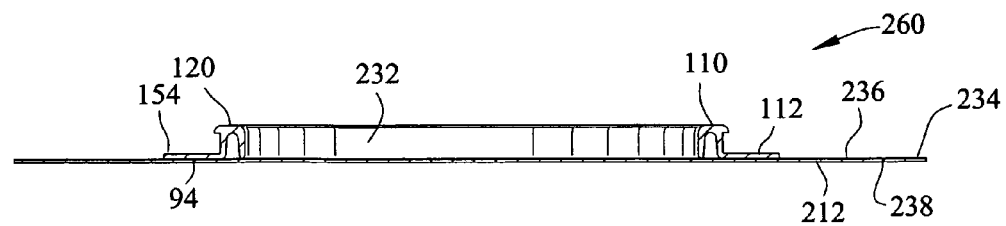
FIG. 39 is a sectional view along line 39-39 in FIG. 36.
Figure 40:
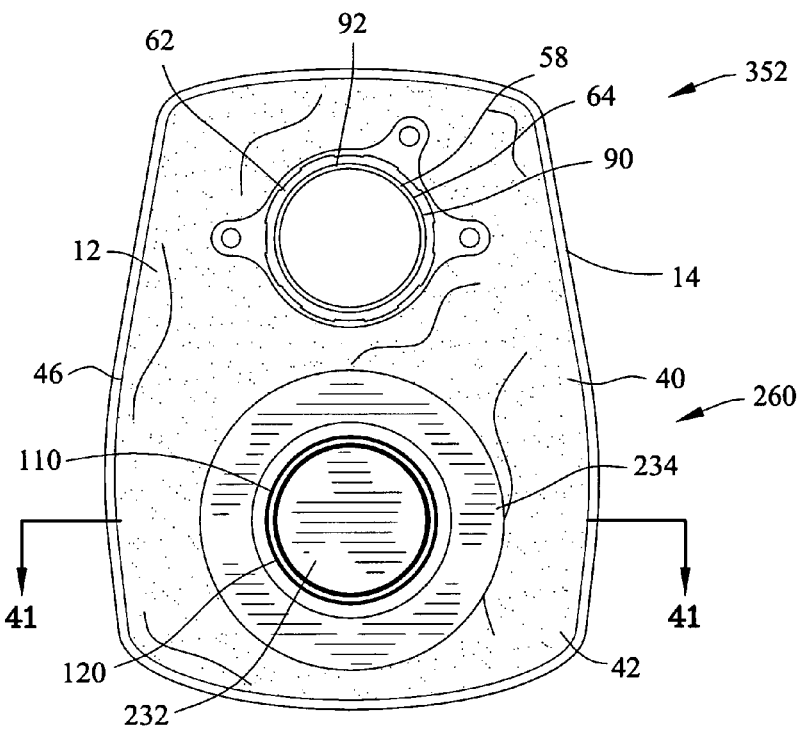
FIG. 40 is a view similar to FIG. 3 illustrating the ostomy closure of FIG. 36 wherein a cap adhesive layer temporarily securing the ostomy closure to the ostomy pouch.
Figure 41:
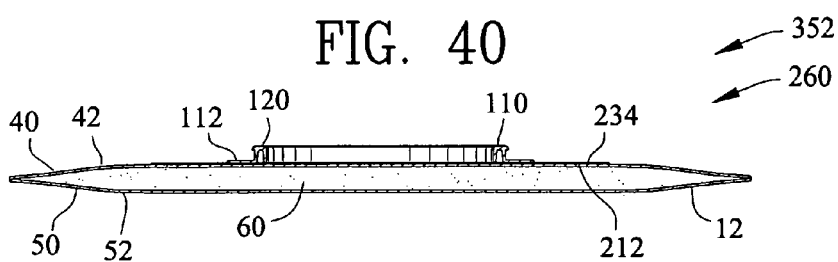
FIG. 41 is a sectional view along line 41-41 in FIG. 40.
Figure 42:
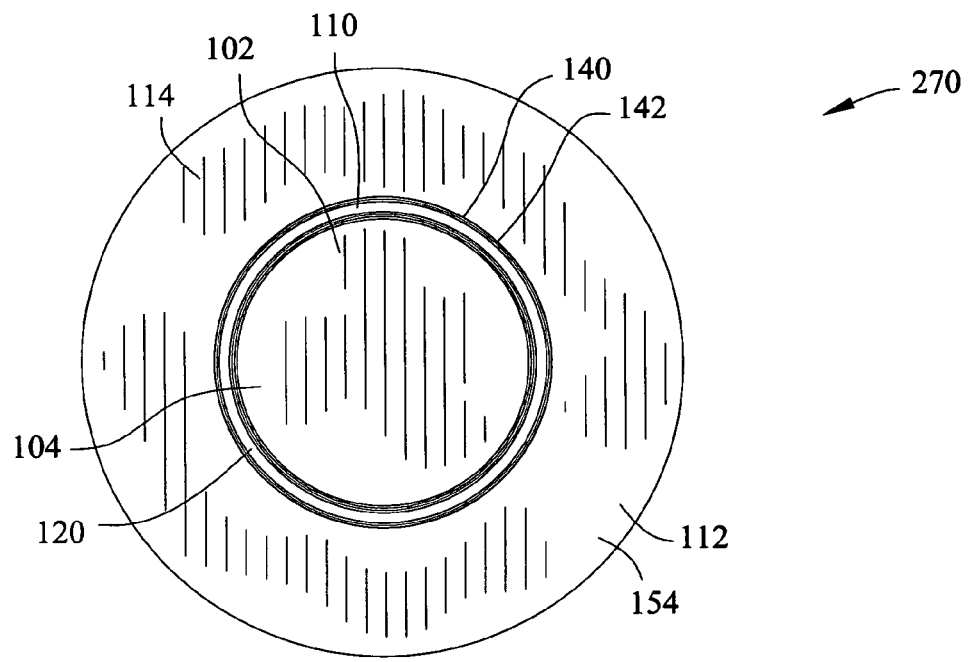
FIG. 42 is a top view of a seventh embodiment for an ostomy closure including a flexible storage bag coupled to the ostomy closure.
Figure 43:
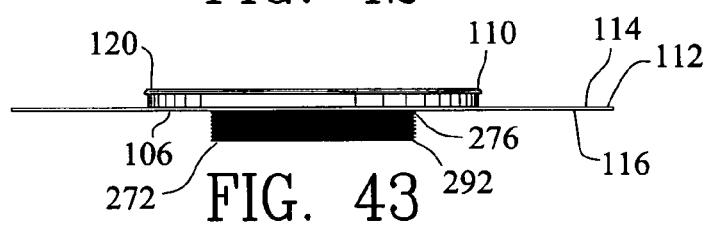
FIG. 43 is a side view of FIG. 42.
Figure 44:
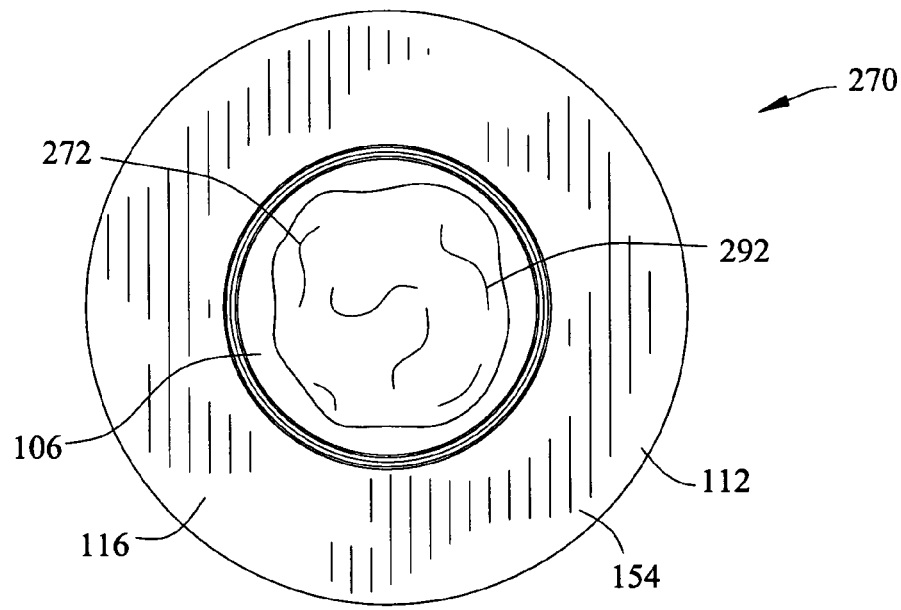
FIG. 44 is a bottom view of FIG. 42.

As shown in FIG. 6, the cap flange 110 couples with the pouch flange 62 for positioning the cap body 102 over the pouch orifice 64 and defining a sealing closure 150. More specifically, the pouch seal rim 72 and surface 72, the first linear member and surface 74, the primary arcuate member and surface 76, the second linear member and surface 78, and the secondary arcuate member and surface 80 of the pouch sealing member 66 seat against the interior surface 104 of the cap body 102, a third linear member and surface 126, a major arcuate member and surface 128, a fourth linear member and surface 130, to a minor arcuate member and surface 132 of the cap sealing member 120 respectively. The sealing closure 150 maintains the stool 36 and the stool odor 38 within the ostomy chamber 60.

Upon the cap flange 110 fully coupling with the pouch flange 62, the cap locking member 122 engages with the pouch locking member 68 for defining a locking closure 152. More specifically, the main linear lock member 86 and the main arcuate lock member 88 of the first locking tab 84 locks against the minor linear lock member 136 and the minor arcuate lock member 138 of the second locking tab 134 respectively. The locking closure 152 prevents inadvertent removal of the cap flange 110 from the pouch flange 62. Preferably, the cap body 102, the cap flange 110 and the cap lip 112 define a unitary-one-piece unit 154 constructed from injected molding process.

FIGS. 14-21 illustrate a second embodiment 170 of the ostomy closure 10 for maintaining the stool 36 and the stool odor 38 within the ostomy chamber 60. The second embodiment 170 of the ostomy closure 10 includes the interior surface 114 of the cap lip 112 including a first aligning tab 172, a second aligning tab 174, a third aligning tab 176 and a four aligning tab 178 positioning adjacent to the cap flange 110. Preferably, the first aligning tab 172, the second aligning tab 174, the third aligning tab 176 and the four aligning tab 178 defining an equidistance orientation 180 about the cap flange 110. Each of the first, second, third and fourth aligning tabs 172, 174, 176 and 178 include a generally n-shaped aligning member 182. More specifically, the first, second, third and fourth aligning tabs 172, 174, 176 including a first linear aligning member and surface 184 extending perpendicularly from the interior surface 114 of the cap lip 112, an aligning arcuate member and surface 186 and a second linear aligning member and surface 188 extending non-perpendicularly from the interior surface 114 of the cap lip 112.

The first aligning tab 172, the second aligning tab 174, the third aligning tab 176 and the four aligning tab 178 and the cap flange 110 define a first aligning channel 190, a second aligning channel 192, a third aligning channel 194 and a fourth aligning channel 196 respectively for centering the cap flange 110 relative to the pouch flange 62 prior to the cap flange 110 coupling within the pouch flange 62. More specifically, the pouch flange 62 is inserted into the first aligning channel 190, the second aligning channel 192, the third aligning channel 194 and/or the fourth aligning channel 196 to facilitate the alignment between the cap flange 110 and the pouch flange 62 and expedite the sealing closure 150 and locking closure 152. Preferably, the cap body 102, the cap flange 110 and the cap lip 112 define a unitary-one-piece unit 154 constructed from injected molding process.

FIGS. 22-27 illustrate a third embodiment 210 of the ostomy closure 10 for maintaining the stool 36 and the stool odor 38 within the ostomy chamber 60. The third embodiment 210 of the ostomy closure 10 includes the exterior surface 106 of the cap body 102 having a cap adhesive layer 212 for temporarily securing the cap body 102 to the ostomy pouch 12. Furthermore, the exterior surface 116 of the cap lip 112 may have a second cap adhesive layer 214 for temporarily securing the cap body 102 to the ostomy pouch 12. The first and second cap adhesive layer 212 and 214 may be utilized for positioning the cap body 102 to the exterior surface 42 of the first flexible layer 40 while the ostomy pouch 12 is engaged with the plate flange 24. After the ostomy pouch 12 is disengaged from the plate flange 24, the individual 32 may promptly remove the cap body 102 from the ostomy pouch 12 for engaging the cap body 102 with the pouch flange 62.

FIGS. 28-32 illustrate a fourth embodiment 230 of the ostomy closure 10 for maintaining the stool 36 and the stool odor 38 within the ostomy chamber 60. The fourth embodiment 230 of the ostomy closure 10 includes the cap flange 110 defining a cap flange aperture 232. A flexible sheet 234 defines an interior surface 236 and an exterior surface 238. The interior surface 236 of the flexible sheet 234 is coupled to the cap flange 110 for covering the cap flange aperture 232. The cap flange 110 couples with the pouch flange 62 for positioning the flexible sheet 234 over the pouch orifice 64 and defining the sealing closure 150. The sealing closure 150 maintains the stool 36 and the stool odor 38 within the ostomy chamber 60. The cap locking member 122 engages with the pouch locking member 68 for defining a locking closure 152. The locking closure 152 prevents inadvertent removal of the cap flange 110 from the pouch flange 62. Preferably, the cap flange 62 and the cap lip 112 defining a unitary-one-piece unit 154 constructed from injected molding process. The cap flange 62 and the flexible sheet 234 may be coupled by a heat sealing, gluing or other coupling means 94.

FIGS. 33-35 illustrate a fifth embodiment 250 of the ostomy closure 10 for maintaining the stool 36 and the stool odor 38 within the ostomy chamber 60. The fifth embodiment 250 of the ostomy closure 10 combines the second embodiment 170 in FIGS. 14-21 with the fourth embodiment 230 of FIGS. 28-32.

FIGS. 36-41 illustrate a sixth embodiment 260 of the ostomy closure 10 for maintaining the stool 36 and the stool odor 38 within the ostomy chamber 60. The sixth embodiment 260 of the ostomy closure 10 combines the third embodiment 210 of FIGS. 22-27 with the fourth embodiment 230 of FIGS. 28-32.

FIGS. 42-49 illustrate a seventh embodiment 270 of the ostomy closure 10 for maintaining the stool 36 and the stool odor 38 within the ostomy chamber 60. The seventh embodiment 270 of the ostomy closure 10 a flexible storage bag 272 having an enclosure body 274 extending between a bag base 267 and a bag opening 278. The enclosure body 274 defining a bag chamber 280. Preferably, the flexible storage bag 272 is constructed of a polymeric material.

Figure 46:
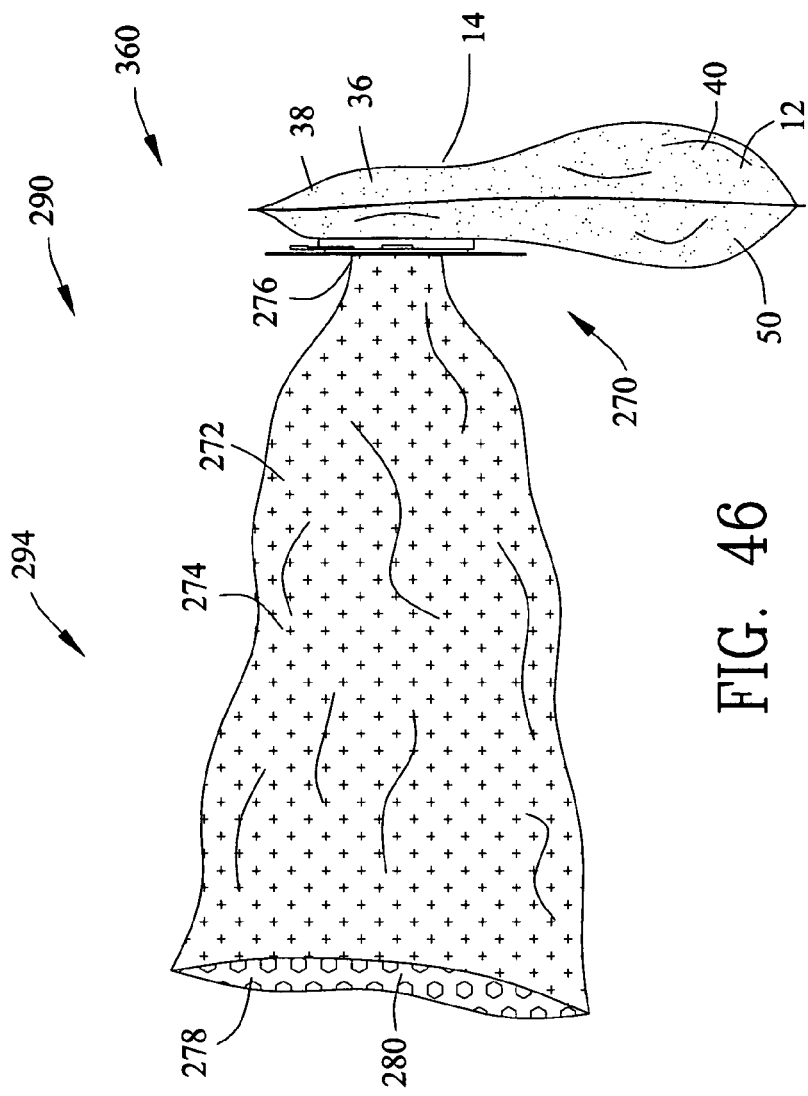
FIG. 46 is a view similar to FIG. 45 illustrating the flexible storage bag expanding the flexible storage bag from the ostomy closure.
Figure 45:
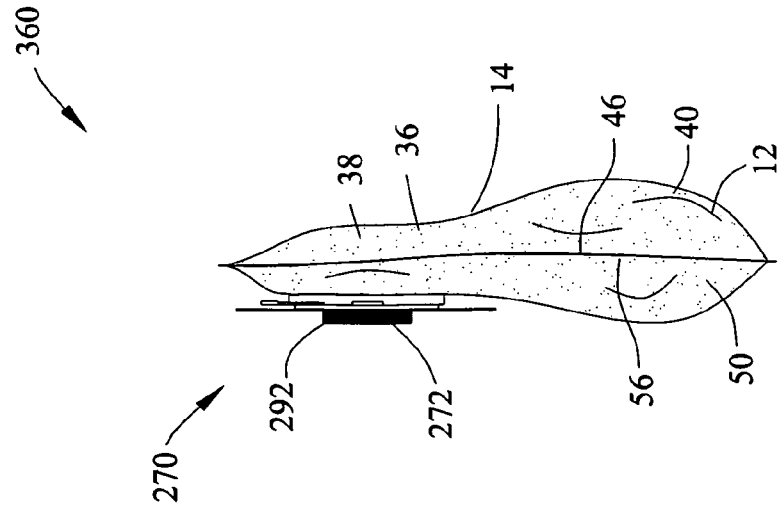
FIG. 45 is a side elevational view of the ostomy closure of FIG. 42 engaged with the ostomy pouch.

The bag base 276 is coupled to either the exterior surface 106 of the cap body 102 as shown in the first embodiment of FIGS. 2-13 or to the exterior surface 238 of the flexible sheet 234 as shown in the fourth embodiment of FIGS. 28-32. The flexible sheet 234 and cap flange 110 define a cap and bag single unit 290. As shown in FIG. 45, the enclosure body 274 may be compacted by folding, vacuum forming or other means adjacent to the exterior surface 106, 238 of either the cap body 102 or the exterior surface 238 for defining a temporary compact cap and bag unit 292. As shown in FIG. 46, the enclosure body 274 may be subsequently expanded from the exterior surface 106, 238 for defining a deployed cap and bag unit 294. As shown in FIG. 47, the bag opening 278 may then be retracted over the flexible storage bag 272 for defining an inverted flexible storage bag 296. As shown in FIG. 48, upon further retraction of the flexible storage bag 272, the bag opening 278 is retracting over the cap flange 110 for defining a bag cap enclosure 298. FIG. 48 also illustrates the bag opening 278 retracting over the ostomy pouch 12 for defining a bag pouch enclosure 300. As shown in FIG. 49, a bag closure 302 engages the enclosure body 274 for encapsulating both the cap flange 110 and the ostomy pouch 12 within the bag chamber 280. The bag closure 302 may include a drawstring closure, knot, zip lock, adhesive or other fastening means. The flexible storage bag 272 maintains the stool 36 and the stool odor 38 within the bag chamber 280 if the cap sealing member 120 is inadvertently ruptured.

FIGS. 50-53 illustrate an eighth embodiment 318 of the ostomy closure 10 for maintaining the stool 36 and the stool odor 38 within the ostomy chamber 60. The eighth embodiment 318 of the ostomy closure 10 includes a sheet of ostomy closures 320 for sealing a plurality of ostomy pouches 12. The sheet of ostomy closures 320 comprises a plurality of cap bodies 102 defining an interior surface 104 and an exterior surface 106 extending to a peripheral edge 108. The plurality of cap flanges 110 are coupled to the peripheral edge 108 of the plurality of cap bodies 102 and extend from the interior surface 104 of the plurality of cap bodies 102. The plurality of cap locking members 122 are integral to the plurality of cap flanges 110. The plurality of cap lips 112 define an interior surface 114 and an exterior surface 116 extending from the plurality of cap flanges 110 for manipulating the plurality of cap bodies 102 and the plurality of cap flanges 110.

A perforated edge 324 traverse the plurality of cap bodies 102 for assisting in the separation of each of the plurality of cap bodies 102. Each of the plurality of cap flanges 110 couple with the pouch flange 62 for positioning each of the plurality of cap bodies 102 over the pouch orifice 64 and define a sealing closure 150. The sealing closure 150 maintains the stool 36 and the stool odor 38 within the ostomy chamber 60. Each of the plurality of cap locking members 122 engage with the pouch locking member 68 for defining a locking closure 152. The locking closure 152 prevents inadvertent removal of the plurality of cap flanges 110 from the pouch flange 62.

As shown in FIG. 53, the exterior surface 106 of the plurality of cap bodies 102 may include the cap adhesive layer 212 for temporarily securing each of the plurality of cap bodies 102 to the ostomy pouch 12. An adhesive backing sheet 322 is secured to the cap adhesive layer 212 for protecting and preventing unwanted adhesion to the cap adhesive layer 212. The sheet of ostomy closures 320 may further include a plurality of flexible storage bags 272 as shown in FIGS. 42-49 for the seventh embodiment 270 engaging each of either the plurality of cap bodies 102 or the plurality of flexible sheets 234.

The present invention further incorporates a method for utilizing an ostomy closure 10 for sealing an ostomy pouch 12. The method comprising the steps of first disengaging 340 the pouch locking member 68 from the plate locking member 26 as shown in FIG. 2. A further step includes disengaging 342 the pouch flange 62 from the plate flange 24 as shown in FIG. 2.

The method may further include the step of removing 352 the cap body 102 from the ostomy pouch 12 that is temporarily secured by the cap adhesive layer 212 as shown in FIGS. 26, 27, 40 and 41. FIGS. 19 and 20 illustrate a possible further step wherein the individual 32 centers 350 the aligning channel 190 relative to the cap flange 110 for centering the cap flange 110 relative to the pouch flange 62 prior to the cap flange 110 coupling within the pouch flange 62. FIGS. 19-21 illustrate the step of engaging 344 the cap flange 110 with the pouch flange 62 for positioning a cap body 102 over the pouch orifice 64 and maintaining the stool 36 and the stool odor 38 within the ostomy chamber 60. A further step includes engaging the cap locking member 122 with the pouch locking member 68 as shown in FIGS. 20 and 21 for preventing inadvertent removal of the cap flange 110 from the pouch flange 62.

FIGS. 45 and 46 illustrate a possible further step wherein the flexible storage bag 272 is expanded 360 from either the cap body 102 or the flexible sheet 234. A further step includes retracting 362 the bag opening 278 of the flexible storage bag 272 over the flexible storage bag 272 as shown in FIG. 47. As shown in FIG. 48, the enclosure body 274 may be further retracted 364 in which the bag opening 278 traverses over the cap flange 110. As also illustrated in FIG. 48, the enclosure body 274 may be further retracted 366 in which the bag opening 278 traverses over the ostomy pouch 12. Thereafter, the method may include sealing 368 the flexible storage bag 272 for encapsulating both the cap flange 110 and the ostomy pouch 12 within the bag chamber 280 as shown in FIG. 49. The flexible storage bag 272 maintains the stool 36 and the stool odor 38 within the bag chamber 280 if the cap sealing member 120 is inadvertently ruptured.

The present disclosure includes that contained in the appended claims as well as that of the foregoing description. Although this invention has been described in its preferred form with a certain degree of particularity, it is understood that the present disclosure of the preferred form has been made only by way of example and that numerous changes in the details of construction and the combination and arrangement of parts may be resorted to without departing from the spirit and scope of the invention.

What is claimed is:

1. An ostomy device comprising:
an ostomy pouch having a first flexible layer with an exterior surface and an interior surface extending together to a first layer edge and a second flexible layer with an exterior surface and an interior surface extending together to a second layer edge, the first layer edge and the second layer edge being coupled together to define an ostomy chamber, wherein:
the first flexible layer includes a single aperture extending through its interior surface and exterior surface to provide access to the ostomy chamber and the second flexible layer includes no aperture extending through its interior surface and exterior surface to provide access to the ostomy chamber,
and
the ostomy pouch includes a pouch flange secured to the first flexible layer and forming a pouch orifice aligned with the single aperture in the first flexible layer, the pouch flange providing a pouch sealing member and a pouch locking member integral to the pouch flange;
and
an ostomy closure having a cap body defining an interior surface and an exterior surface, a cap flange coupled to the cap body and extending from the interior surface of the cap body, a cap sealing member and a cap locking member integral to the cap flange, and a cap lip defining an interior surface and an exterior surface and extending outward from the cap flange for manipulating the cap body and the cap flange,
wherein:
the ostomy closure and the ostomy pouch are separate components not formed integrally with one another, and
the ostomy closure is connected to and in contact with the pouch flange only when the ostomy closure is positioned over the single aperture in the first flexible layer and the cap flange is coupled with the pouch flange to define a sealing closure.

2. The ostomy device of claim 1, wherein the cap body, the cap flange and the cap lip define a unitary-one-piece unit constructed from an injected molding process.

3. The ostomy device of claim 1, wherein the interior surface of the cap lip includes an aligning tab positioned adjacent to the cap flange, the aligning tab and the cap flange defining an aligning channel there between for centering the cap flange relative to the pouch flange prior to the cap flange being coupled with the pouch flange.

4. The ostomy device of claim 1, wherein the interior surface of the cap lip includes a first aligning tab, a second aligning tab, a third aligning tab and a fourth aligning tab positioned adjacent to the cap flange, the first aligning tab, the second aligning tab, the third aligning tab and the fourth aligning tab defining an equidistance orientation about the cap flange; the first aligning tab, the second aligning tab, the third aligning tab and the fourth aligning tab and the cap flange defining a first aligning channel, a second aligning channel, a third aligning channel and a fourth aligning channel respectively for centering the cap flange relative to the pouch flange prior to the cap flange being coupled with the pouch flange.

5. The ostomy device of claim 1, wherein the exterior surface of the cap body includes a cap adhesive layer for temporarily securing the ostomy closure to the ostomy pouch.

6. The ostomy device of claim 1, wherein the exterior surface of the cap body and the exterior surface of the cap lip include a cap adhesive layer for temporarily securing the ostomy closure to the ostomy pouch.

7. An ostomy device comprising:
an ostomy pouch having a first flexible layer with an exterior surface and an interior surface extending together to a first layer edge and a second flexible layer with an exterior surface and an interior surface extending together to a second layer edge, the first layer edge and the second layer edge being coupled together to define an ostomy chamber, wherein:
the first flexible layer includes a single aperture extending through its interior surface and exterior surface to provide access to the ostomy chamber and the second flexible layer includes no aperture extending through its interior surface and exterior surface to provide access to the ostomy chamber,
and
the ostomy pouch includes a pouch flange secured to the first flexible layer and forming a pouch orifice aligned with the single aperture in the first flexible layer, the pouch flange providing a pouch sealing member and a pouch locking member integral to the pouch flange; and
an ostomy closure having a cap flange defining a cap flange aperture, a cap locking member integral to the cap flange, a cap lip defining an interior surface and an exterior surface extending from the cap flange, a flexible sheet defining an interior surface and an exterior surface; the interior surface of the flexible sheet being coupled to the cap flange for covering the cap flange aperture, wherein:
the cap locking member engages with the pouch locking member to define a locking closure, the locking closure preventing inadvertent removal of the cap flange from the pouch flange,
the ostomy closure and the ostomy pouch are separate components not formed integrally with one another,
and
the ostomy closure is connected to and in contact with the pouch flange only when the ostomy closure is positioned over the single aperture in the first flexible layer and the cap flange is coupled with the pouch flange to define a sealing closure.

8. The ostomy device of claim 7, wherein the cap flange and the cap lip define a unitary-one-piece unit constructed from an injected molding process; and the cap flange and the flexible sheet are coupled by a heat seal couple.

9. The ostomy device of claim 7, wherein the interior surface of the cap lip includes an aligning tab positioned adjacent to the cap flange, the aligning tab and the cap flange defining an aligning channel there between for centering the cap flange relative to the pouch flange prior to the cap flange being coupled with the pouch flange.

10. The ostomy device of claim 7, wherein the interior surface of the cap lip includes a first aligning tab, a second aligning tab, a third aligning tab and a fourth aligning tab positioned adjacent to the cap flange, the first aligning tab, the second aligning tab, the third aligning tab and the fourth aligning tab defining an equidistance orientation about the cap flange, the first aligning tab, the second aligning tab, the third aligning tab and the fourth aligning tab and the cap flange defining a first aligning channel, a second aligning channel, a third aligning channel and a fourth aligning channel respectively for centering the cap flange relative to the pouch flange prior to the cap flange being coupled with the pouch flange.

11. The ostomy device of claim 7, wherein the exterior surface of the flexible sheet including a cap adhesive layer for temporarily securing the flexible sheet and the cap flange to the ostomy pouch.

12. An ostomy device comprising:
an ostomy pouch having a first flexible layer with an exterior surface and an interior surface extending together to a first layer edge and a second flexible layer with an exterior surface and an interior surface extending together to a second layer edge, the first layer edge and the second layer edge being coupled together to define an ostomy chamber, wherein:
the first flexible layer includes a single aperture extending through its interior surface and exterior surface to provide access to the ostomy chamber and the second flexible layer includes no aperture extending through its interior surface and exterior surface to provide access to the ostomy chamber,
and
the ostomy pouch includes a pouch flange secured to the first flexible layer and forming a pouch orifice aligned with the single aperture in the first flexible layer, the pouch flange providing a pouch sealing member and a pouch locking member integral to the pouch flange;
and
an ostomy closure having a cap body defining an interior surface and an exterior surface, a cap flange coupled to the cap body and extending from the interior surface of the cap body, a cap sealing member and a cap locking member integral to the cap flange, and a cap lip defining an interior surface and an exterior surface and extending outward from the cap flange for manipulating the cap body and the cap flange,
wherein:
the ostomy closure and the ostomy pouch are separate components not formed integrally with one another,
the ostomy closure is connected to and in contact with the pouch flange only when the ostomy closure is positioned over the single aperture in the first flexible layer and the cap flange is coupled with the pouch flange to define a sealing closure, and
the ostomy closure further includes a flexible storage bag having an enclosure body extending between a bag base and a bag opening, the enclosure body defining a bag chamber, the bag base coupling to the exterior surface of the cap body for defining a cap and bag single unit, the bag opening retracting over the flexible storage bag for defining an inverted flexible storage bag, the bag opening retracting over the cap body for defining a bag cap enclosure, the bag opening retracting over the ostomy pouch for defining a bag pouch enclosure and a bag closure engaging the enclosure body for encapsulating both the ostomy closure and the ostomy pouch within the bag chamber.

13. The ostomy device of claim 12, wherein the enclosure body compacting adjacent to the exterior surface of the cap body for defining a temporary compact cap and bag unit, the enclosure body expanding from the exterior surface of the cap body for defining a deployed cap and bag unit.

14. An ostomy device comprising:
an ostomy pouch having a first flexible layer with an exterior surface and an interior surface extending together to a first layer edge and a second flexible layer with an exterior surface and an interior surface extending together to a second layer edge, the first layer edge and the second layer edge being coupled together to define an ostomy chamber, wherein:
the first flexible layer includes a single aperture extending through its interior surface and exterior surface to provide access to the ostomy chamber and the second flexible layer includes no aperture extending through its interior surface and exterior surface to provide access to the ostomy chamber,
and
the ostomy pouch includes a pouch flange secured to the first flexible layer and forming a pouch orifice aligned with the single aperture in the first flexible layer, the pouch flange providing a pouch sealing member and a pouch locking member integral to the pouch flange;
an ostomy closure having a cap flange defining a cap flange aperture, a cap locking member integral to the cap flange, a cap lip defining an interior surface and an exterior surface extending from the cap flange, a flexible sheet defining an interior surface and an exterior surface, the interior surface of the flexible sheet being coupled to the cap flange for covering the cap flange aperture, wherein:
the cap locking member engages with the pouch locking member to define a locking closure, the locking closure preventing inadvertent removal of the cap flange from the pouch flange,
the ostomy closure and the ostomy pouch are separate components not formed integrally with one another,
the ostomy closure is connected to and in contact with the pouch flange only when the ostomy closure is positioned over the single aperture in the first flexible layer and the cap flange is coupled with the pouch flange to define a sealing closure,
and
the ostomy closure further includes a flexible storage bag having an enclosure body extending between a bag base and a bag opening, the enclosure body defining a bag chamber, the bag base coupling to the exterior surface of the cap body for defining a cap and bag single unit, the bag opening retracting over the flexible storage bag for defining an inverted flexible storage bag, the bag opening retracting over the cap body for defining a bag cap enclosure, the bag opening retracting over the ostomy pouch for defining a bag pouch enclosure and a bag closure engaging the enclosure body for encapsulating both the cap body and the ostomy pouch within the bag chamber.

15. The ostomy device of claim 14, wherein the enclosure body compacts adjacent to the exterior surface of the flexible sheet to define a temporary compact cap and bag unit; and
the enclosure body expanding from the exterior surface of the flexible sheet to define a deployed cap and bag unit.

16. A pouch and closure for deposing stool from an individual, the pouch and closure comprising:
an ostomy pouch having a first flexible layer coupling to a second flexible layer for defining an ostomy chamber, the first flexible layer including a single aperture to provide access to the ostomy chamber and the second flexible layer including no aperture, a pouch flange securing to the first flexible layer, a pouch locking member integral to the pouch flange, a pouch orifice positioning within the pouch flange and aligning with the single aperture in the first flexible layer;
and
an ostomy closure having a cap body defining an interior surface and an exterior surface extending to a peripheral edge, a cap flange coupling to the peripheral edge of the cap body and extending from the interior surface of the cap body, a cap locking member integral to the cap flange, a cap lip defining an interior surface and an exterior surface extending from the cap flange for manipulating the cap body and the cap flange, wherein:
the ostomy closure is connected to and in contact with the pouch flange only when the ostomy closure is positioned over the single aperture in the first flexible layer and the cap flange is coupled with the pouch flange to define a sealing closure.

17. A pouch and closure for deposing stool from an individual, the pouch and closure comprising:
an ostomy pouch having a first flexible layer coupling to a second flexible layer for defining an ostomy chamber, the first flexible layer including a single aperture to provide access to the ostomy chamber, a pouch flange securing to the first flexible layer, a pouch locking member integral to the pouch flange a pouch orifice positioning within the pouch flange and aligning with the single aperture and traversing the first flexible layer for conveying stool from the individual to the ostomy chamber;
and
an ostomy closure having a cap body defining an interior surface and an exterior surface, a cap flange coupling to the cap body and extending from the interior surface of the cap body a cap locking member integral to the cap flange and a cap lip defining an interior surface and an exterior surface extending from the cap flange for manipulating the cap body and the cap flange, wherein:
the ostomy closure and the ostomy pouch are separate components not formed integrally with one another,
and
the ostomy closure is connected to and in contact with the pouch flange only when the ostomy closure is positioned over the pouch orifice in the first flexible layer and the cap flange is coupled with the pouch flange to define a sealing closure.

* * * * *